United States Patent
Brosso et al.

(10) Patent No.: US 12,201,624 B2
(45) Date of Patent: Jan. 21, 2025

(54) COMPOSITIONS COMPRISING MIXTURES OF COMPOUNDS AND USES THEREOF

(71) Applicant: Prostasis, LLC, Malvern, PA (US)

(72) Inventors: Mark Brosso, Malvern, PA (US); Nicholas Allen Moore, Chester (GB)

(73) Assignee: Prostasis, LLC, Malvern, PA (US)

( * ) Notice: Subject to any disclaimer, the term of this patent is extended or adjusted under 35 U.S.C. 154(b) by 0 days.

(21) Appl. No.: 18/316,444

(22) Filed: May 12, 2023

(65) Prior Publication Data

US 2023/0277520 A1 Sep. 7, 2023

Related U.S. Application Data

(63) Continuation of application No. 17/747,440, filed on May 18, 2022, now Pat. No. 11,684,618.

(60) Provisional application No. 63/189,963, filed on May 18, 2021.

(51) Int. Cl.
| | | |
|---|---|---|
| *A61K 31/455* | (2006.01) | |
| *A61K 31/145* | (2006.01) | |
| *A61K 31/357* | (2006.01) | |
| *A61K 31/385* | (2006.01) | |
| *A61K 31/4375* | (2006.01) | |
| *A61K 47/54* | (2017.01) | |
| *A61P 3/04* | (2006.01) | |

(52) U.S. Cl.
CPC .......... *A61K 31/455* (2013.01); *A61K 31/145* (2013.01); *A61K 31/357* (2013.01); *A61K 31/385* (2013.01); *A61K 31/4375* (2013.01); *A61K 47/544* (2017.08); *A61P 3/04* (2018.01)

(58) Field of Classification Search
CPC .. A61K 31/455; A61K 47/544; A61K 31/145; A61K 31/357; A61K 31/385; A61K 31/4375; A61P 3/04
USPC ....................................................... 514/356
See application file for complete search history.

(56) References Cited

U.S. PATENT DOCUMENTS

| | | |
|---|---|---|
| 4,764,508 A | 8/1988 | Gabetta et al. |
| 9,566,309 B2 | 2/2017 | Bombardelli et al. |
| 11,684,618 B2 | 6/2023 | Brosso et al. |
| 2010/0086627 A1 | 4/2010 | Zabrecky |
| 2019/0328758 A1 | 10/2019 | Alvarez et al. |
| 2020/0397807 A1 | 12/2020 | Pranesh et al. |

OTHER PUBLICATIONS

Glossary of Medical Education Terms. Institute for International Medical Education (IIME). https://www.iime.org/glossary.htm#P (accessed on Apr. 20, 24) (Year: 2024).*
Noori et al. Role of natural products for the treatment of Alzheimer's disease. European Journal of Pharmacology 898 (2021) 173974, pp. 1-16. (Year: 2021).*
Tabatabaei-Malazy et al. Targeting metabolic disorders by natural products. Journal of Diabetes & Metabolic Disorders (2015) 14:57, pp. 1-21. (Year: 2015).*
Anonymous "7-Day ReduceXS Total Body Cleansing Program", Mar. 30, 2021, 3 pages, retrieved from the Internet at http://images.salsify.com/image/upload/s--4cjq1dbl--/1idewgxm6hls7lcvswkq.pdf.
International Search Report and Written Opinion for International Application No. PCT/US2022/029804, mailed Aug. 19, 2022, 21 pages.
Knouff, et al., "Apo E structure determines VLDL clearance and atherosclerosis risk in mice," J. Clin. Invest. 1999, 103(11):1579-1586.
Pankiewicz, et al., "APOE Genotype Differentially Modulates Effects of Anti-Aβ, Passive Immunization in APP Transgenic Mice," Molecular Neurodegeneration, 2017, 12(12):1-17.
Semalty, et al., "Supramolecular phospholipids-polyphenolics interactions: The PHYTOSOME® strategy to improve the bioavailability of phytochemicals," Fitoterapia, 2010, 81:306-314.
Siliphos® Silybin Phytosome®, Healthy Liver, indena S.p.A., 2019, 1-2.
Sullivan, et al., "Targeted Replacement of the Mouse Apolipoprotein E Gene with the Common Human APOE3 Allele Enhances Diet-induced Hypercholesterolemia and Atherosclerosis," The Journal of Biological Chemistry, 1997, 272(29):17972-17980.

* cited by examiner

*Primary Examiner* — Yih-Horng Shiao
(74) *Attorney, Agent, or Firm* — COOLEY LLP

(57) ABSTRACT

Provided herein are compositions comprising niacin, berberine, one or more of silymarin, silibinin, and Siliphos®, lipoic acid, taurine, and phosphatidylcholine. Such compositions are useful for treating or preventing obesity, metabolic and hepatic and neurodegenerative disorders.

22 Claims, 20 Drawing Sheets

COMPOSITIONS COMPRISING MIXTURES OF COMPOUNDS AND USES THEREOF

CROSS-REFERENCE TO RELATED APPLICATIONS

This application is a continuation of U.S. patent application Ser. No. 17/747,440, filed May 18, 2022 and issued as U.S. Pat. No. 11,684,618, which claims priority to U.S. Provisional Patent Application No. 63/189,963, filed May 18, 2021, the contents of each of which are incorporated by reference herein in their entireties for all purposes.

TECHNICAL FIELD

The disclosure relates to compositions comprising mixtures of naturally occurring compounds and uses of such compositions.

BACKGROUND

People in developed countries are living significantly longer than they were years ago. This has created a rapidly increasing society of elderly persons with concomitant increases in diseases of the aged. As the population ages, those experiencing cognitive decline due to neurodegeneration has significantly increased. An age-related loss of neuronal function increases the incidence of dementia. The economic and social burdens accelerate as dementia sufferers require constant care and assistance with the most basic activities of daily living. Among causes of dementia, Alzheimer's disease (AD) is the most common. AD is also a common cause of mortality and is now the sixth-leading cause of death as well as the fastest growing leading cause of death in the United States. As populations in the United States and in developed countries continue to age, more people are living beyond the age of 80. AD rates are estimated to be as high as 50% for persons 80 years of age or greater. Without the discovery of disease modifying treatments for AD, an increasing elderly population are expected triple the worldwide prevalence of AD by 2040. These statistics highlight the need to find effective methods for maintaining cognition and preventing AD. Current treatments provide only temporary relief of the symptoms associated with dementia and do not modify the underlying course of the disease.

Obesity is a major global health problem and rates of obesity (body mass index (BMI) >30 kg/m$^2$) have risen steadily. Recent figures show an incidence of obesity of more than 1 in 4 in many parts of the US. These high rates are similar in other developed countries, and the incidence of weight gain is increasing in less developed regions. Obesity is not just a cosmetic or lifestyle illness but leads to many life-threatening health complications. As the BMI increases, the incidence of metabolic disorders (e.g., Type 2 diabetes, hypertension, non-alcoholic steatohepatitis (NASH)) and associated musculoskeletal problems increase.

There is a need for compositions to treat, reduce symptoms, or improve outcomes related to neurodegeneration, dementia, obesity, hepatic and metabolic disorders.

SUMMARY

Provided herein is a composition comprising: (a) niacin, or a pharmaceutically acceptable salt thereof; (b) berberine, or a pharmaceutically acceptable salt thereof; (c) sylimarin, silibinin, or Siliphos®, or any combination thereof, or a pharmaceutically acceptable salt thereof; (d) lipoic acid, or a pharmaceutically acceptable salt thereof; (e) taurine, or a pharmaceutically acceptable salt thereof; and (f) phosphatidylcholine or a pharmaceutically acceptable salt thereof.

In some embodiments, the niacin is vitamin B3, nicotinic acid, nicotinamide, inositol hexanicotinate, nicotinic riboside, nicotinamide adenine dinucleotide (NAD) or NADH.

In some embodiments, the berberine or the pharmaceutically acceptable salt thereof is complexed with a phospholipid.

In some embodiments, the phosphatidylcholine, or the pharmaceutically acceptable salt thereof, is in a complex with one or more of: (a) the niacin, or the pharmaceutically acceptable salt thereof; (b) the berberine, or the pharmaceutically acceptable salt thereof; (c) the sylimarin, silibinin, or Siliphos®, or any combination thereof, or the pharmaceutically acceptable salt thereof; (d) the lipoic acid, or the pharmaceutically acceptable salt thereof; and (e) the taurine, or the pharmaceutically acceptable salt thereof.

In some embodiments, the niacin, or the pharmaceutically acceptable salt thereof, is in an amount from about 20% to about 40% by weight.

In some embodiments, the berberine, or the pharmaceutically acceptable salt thereof, is in an amount from about 10% to about 20% by weight.

In some embodiments, the silymarin, or the pharmaceutically acceptable salt thereof, is in an amount from about 8% to about 20% by weight. In some embodiments, the silibinin, or the pharmaceutically acceptable salt thereof, is in an amount from about 8% to about 20% by weight. In some embodiments, the Siliphos®, or the pharmaceutically acceptable salt thereof, is in an amount from about 8% to about 20% by weight.

In some embodiments, the silymarin, or the pharmaceutically acceptable salt thereof, and the silibinin, or the pharmaceutically acceptable salt thereof, combined, are in an amount from about 8% to about 20% by weight. In some embodiments, the silymarin, or the pharmaceutically acceptable salt thereof, and the Siliphos®, or the pharmaceutically acceptable salt thereof, combined, are in an amount from about 8% to about 20% by weight. In some embodiments, the silibinin, or the pharmaceutically acceptable salt thereof, and the Siliphos®, or the pharmaceutically acceptable salt thereof, combined, are in an amount from about 8% to about 20% by weight.

In some embodiments, the silymarin, or the pharmaceutically acceptable salt thereof, the silibinin, or the pharmaceutically acceptable salt thereof, and the Siliphos®, or the pharmaceutically acceptable salt thereof, combined, are in an amount from about 8% to about 20% by weight.

In some embodiments, the lipoic acid, or the pharmaceutically acceptable salt thereof, is in an amount from about 5% to about 15% by weight.

In some embodiments, the taurine, or the pharmaceutically acceptable salt thereof, is in an amount from about 20% to about 35% by weight.

In some embodiments, the phosphatidylcholine, or the pharmaceutically acceptable salt thereof, is in an amount from about 5% to about 20% by weight.

In some embodiments, the composition comprises: (a) about 250 mg niacin, or a pharmaceutically acceptable salt thereof; about 250 mg berberine, or a pharmaceutically acceptable salt thereof; about 150 mg silymarin, silibinin, or Siliphos®, or any combination thereof, or a pharmaceutically acceptable salt thereof; about 150 mg lipoic acid, or a pharmaceutically acceptable salt thereof; and about 375 mg taurine, or a pharmaceutically acceptable salt thereof; (b)

about 500 mg niacin, or a pharmaceutically acceptable salt thereof; about 250 mg berberine, or a pharmaceutically acceptable salt thereof; about 150 mg silymarin, silibinin, or Siliphos®, or any combination thereof, or a pharmaceutically acceptable salt thereof; about 150 mg lipoic acid, or a pharmaceutically acceptable salt thereof; and about 375 mg taurine, or a pharmaceutically acceptable salt thereof; (c) about 1000 mg niacin, or a pharmaceutically acceptable salt thereof; about 500 mg berberine, or a pharmaceutically acceptable salt thereof; about 300 mg silymarin, silibinin, or Siliphos®, or any combination thereof, or a pharmaceutically acceptable salt thereof; about 300 mg lipoic acid, or a pharmaceutically acceptable salt thereof; and about 750 mg taurine, or a pharmaceutically acceptable salt thereof; or (d) about 2000 mg niacin, or a pharmaceutically acceptable salt thereof; about 750 mg berberine, or a pharmaceutically acceptable salt thereof; about 450 mg silymarin, silibinin, or Siliphos®, or any combination thereof, or a pharmaceutically acceptable salt thereof; about 600 mg lipoic acid, or a pharmaceutically acceptable salt thereof; and about 1500 mg taurine, or a pharmaceutically acceptable salt thereof.

In some embodiments of the compositions disclosed herein, the phospholipid is phosphatidylcholine.

In some embodiments, the composition further comprises a pharmaceutically acceptable carrier, diluent, excipient, or flavoring.

Provided herein is a method for preventing or treating obesity in a subject in need thereof, the method comprising administering to the subject an effective amount of a composition disclosed herein.

Provided herein is a method for preventing or treating a symptom of metabolic syndrome in a subject in need thereof, the method comprising administering to the subject an effective amount of a composition disclosed herein. In some embodiments, the symptom of metabolic syndrome is a liver change, insulin sensitivity, glucose sensitivity or lipid regulation.

Provided herein is a method for preventing or treating non-alcoholic fatty liver disease (NAFLD), non-alcoholic steatohepatitis (NASH) or fatty liver in a subject in need thereof, the method comprising administering to the subject an effective amount of a composition disclosed herein.

Provided herein is a method for conferring neuroprotection on a subject in need thereof, the method comprising administering to the subject an effective amount of a composition disclosed herein. In some embodiments, the subject has a neurodegenerative condition, Alzheimer's disease, dementia, senile systemic amyloidosis, amyloidosis, cerebrovascular amyloidosis or cerebral amyloid angiopathy.

Provided herein is a method for treating or preventing a disease of mitochondrial dysfunction in a subject in need thereof, the method comprising administering to the subject an effective amount of a composition disclosed herein. In some embodiments, the disease of mitochondrial dysfunction is Parkinson's disease.

Provided herein is a method for enhancing the efficacy of an anti-obesity agent in a subject in need thereof, the method comprising administering to the subject the anti-obesity agent and an effective amount of a composition disclosed herein.

In some embodiments, a method further comprises determining the genotype of the APOE isoform in the subject before administering the composition to the subject. In some embodiments, the subject has (a) one or two APOE4 alleles; (b) one or two APOE3 alleles; or (c) one or two APOE2 alleles.

In some embodiments, the method further comprises determining the levels of acylcarnitines and/or branch chain amino acids (BCAA) in the subject as an indicator of treatment outcome and/or disease status.

In some embodiments, the composition is orally administered to the subject twice daily, daily, weekly, biweekly, or monthly.

Provided herein is a composition disclosed herein for use as a medicament.

BRIEF DESCRIPTION OF THE DRAWINGS

FIG. 7A depicts the effect of treatment or no treatment (control) on weight loss in PS1E3 mice fed either a HFD or LFD.

FIG. 7B depicts the effect of treatment or no treatment (control) on weight loss in PS1E4 mice fed either a HFD or a LFD.

FIG. 8A depicts the effect of treatment or no treatment (control) on plasma cholesterol levels in PS1E3 mice fed either a HFD or a LFD.

DETAILED DESCRIPTION

Figure 1:
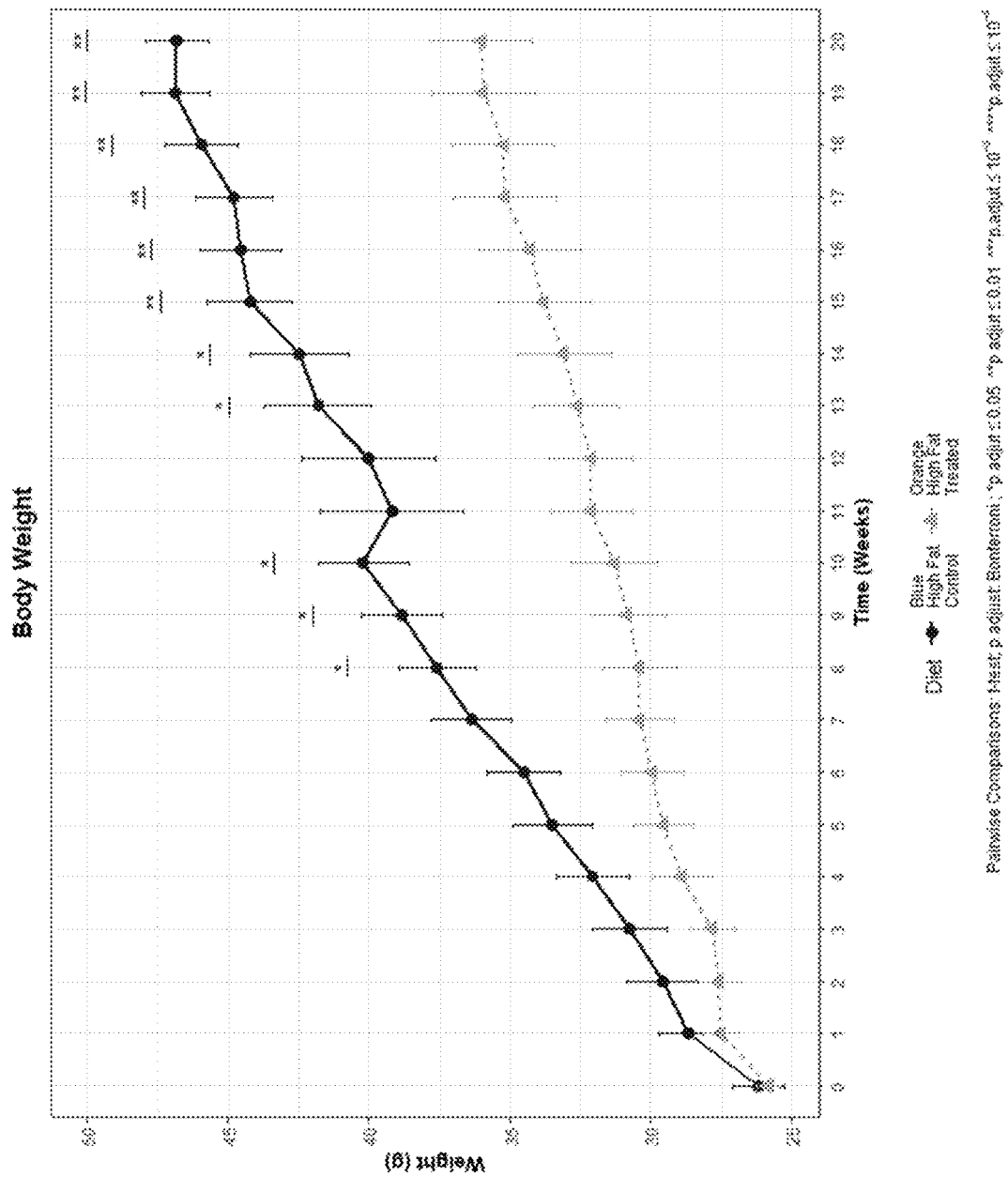
FIG. 1 is a graph depicting the effect of treatment (triangle) on weight gain in wild type mice fed a high-fat diet (HFD) over a 20-week period. Control (circle) mice were fed a HFD but not treated.

The disclosure provides compositions comprising a mixture of compounds ((1) niacin, (2) berberine, (3) taurine, (4) silymarin, silibinin, or Siliphos®, or any combination thereof (5) lipoic acid, and (6) phosphatidylcholine or pharmaceutically acceptable salts of any of the preceding), methods of making the same and methods of using the same. Further provided herein are foodstuffs and beverages comprising the compositions described herein.

As used herein, the singular forms "a," "an," and "the" include plural references unless the context clearly dictates otherwise.

As used herein, the term "about" means ±5% of the value being modified. Thus, "about 1" means from 0.95 to 1.05." As used herein, the term "about" as it is used in a range or a series modifies each member of the range or the series. For example, in the phrases "about 1-5" or "about 1 to 5" the term "about" modifies both the 1 and the 5 as well as the numbers in between 1 and 5. Also, for example, "about 1, 2, 3, 4, or 5" the term "about" modifies each of 1, 2, 3, 4, or 5. Additionally, a range or series that is modified by the term "about" also discloses the same range (including the endpoints) or series not modified by the term "about." For example, the phrase "about 1-5" also discloses the range (including the endpoints) "1-5." Additionally, the phrase a range of "X-Y" is equivalent to "X to Y" and includes the endpoints "X" and "Y." For example, "1-5" is equivalent to "1 to 5."

As used herein, the term "ratio" refers to the amounts of two or more compounds, molecules, and the like, compared to one another. The ratio can be, for example, in terms of absolute weight (e.g., grams to grams; wt:wt). The ratio can be also be, for example, determined by comparing concentrations of each compound (e.g., molarity to molarity; mol: mol). The ratio can also be in terms of moles of each molecule present in the composition. For example, a composition comprising a first and second compound each with 10 mmol would be said to be in a 1 to 1 ratio (i.e., 1.0:1.0).

As used herein, the term "substantially" means at least or greater than 95%.

As used herein, the phrase "recommended daily allowance" or "recommended dietary allowance" refers to an amount to be consumed by an individual that has generally been determined to be desirable. In some embodiments, the individual is a male, female, infant (0-12 months), child (1-10 years), pregnant woman, lactating woman (first 6 months post-partum or 6-12 months post-partum). The male or female can be 11-18 years old or greater than or equal to 19 years old. The recommended daily allowance can be found, for example, in Recommended Dietary Allowances: 10th Edition, Subcommittee on the Tenth Edition of the RDAs, Food and Nutrition Board, Commission on Life Sciences, National Research Council, NATIONAL ACADEMY PRESS, Washington, D.C. 1989, which is hereby incorporated by reference in its entirety. The daily allowances referred to herein and below are determined for a male greater than or equal to 19 years old but can routinely be converted to other types of subjects as needed.

Compositions

Provided herein are compositions comprising (1) niacin, (2) berberine, (3) silymarin, silibinin, or Siliphos®, or any combination thereof, (4) lipoic acid, (5) taurine, and (6) phosphatidylcholine, or pharmaceutically acceptable salts of any of the preceding. In some embodiments, a composition comprises niacin, berberine, one or both of (i) silymarin and (ii) silibinin, lipoic acid, and taurine. Although all the components have been shown to have modest effects on physiological function, the combination of components has a multifaceted action leading to the overall unexpected beneficial effects on neuronal, mitochondrial, hepatic and metabolic function. The weight loss and prevention of weight gain effects of the compositions disclosed herein are independent of food intake and independent of thermogenic/ thermic effects.

Niacin is an essential nutrient found in a wide variety of foods including meats, poultry, and oily fish. Niacin may be vitamin B3, nicotinic acid, nicotinamide, inositol hexanicotinate, nicotinic riboside, nicotinamide adenine dinucleotide (NAD) or NADH. Niacin has anti-inflammatory effects in various tissues including the brain. Niacin deficiency can lead to serious conditions such as pellagra, symptoms of which include diarrhea, inflammation, and cognitive deficits.

In some embodiments, the composition comprises about 100 mg to about 3000 mg mg of niacin (e.g., vitamin B3, nicotinic acid, nicotinamide, inositol hexanicotinate, nicotinic riboside, NAD or NADH), or a pharmaceutically acceptable salt thereof. In some embodiments, the composition comprises about 100, about 150, about 200, about 250, about 300, about 350, about 400, about 450, about 500, about 550, about 600, about 650, about 700, about 750, about 800, about 850, about 900, about 950, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, or about 3000 mg of niacin (vitamin B3, nicotinic acid, nicotinamide, inositol hexanicotinate, nicotinic riboside, NAD or NADH). In some embodiments, the composition comprises about 100 to about 300 mg, about 200 to about 300 mg, about 400 to about 600 mg, about 450 to about 550 mg, about 900 to about 1100 mg, about 950 to about 1150 mg, about 1800 to about 2200 mg, about 1900 to about 2100 mg of niacin (e.g., vitamin B3, nicotinic acid, nicotinamide, inositol hexanicotinate, nicotinic riboside, NAD or NADH), or a pharmaceutically acceptable salt thereof. In some embodiments, the composition comprises about 250, about 500, about 1000, or about 2000 mg of niacin (e.g., vitamin B3, nicotinic acid, nicotinamide, inositol hexanicotinate, nicotinic riboside, NAD or NADH), or a pharmaceutically acceptable salt thereof. In some embodiments, a specified amount of niacin (vitamin B3, nicotinic acid, nicotinamide, inositol hexanicotinate, nicotinic riboside, NAD or NADH), or a pharmaceutically acceptable salt thereof, is combined with the other specified amounts of the individual components described herein.

Berberine is from the protoberberine group of benzylisoquinoline alkaloids found in plants such as *Berberis*, e.g., *Berberis vulgaris* (barberry), *Berberis aristata* (tree turmeric), and others. Berberine is usually found in the roots, rhizomes, stems, and bark. Berberine has been used in Chinese medicine as an antibacterial agent. Berberine is thought to have effects on metabolic function via its effect on AMP-activated protein kinase (AMPK).

In some embodiments, the composition comprises about 100 mg to about 1,500 mg of berberine, or a pharmaceutically acceptable salt thereof. In some embodiments, the composition comprises about 100, about 150, about 200, about 250, about 300, about 350, about 400, about 450, about 500, about 550, about 600, about 650, about 700, about 750, about 800, about 850, about 900, about 950, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, or about 3000 mg of berberine, or a pharmaceutically acceptable salt thereof. In some embodiments, the composition comprises about 100 to about 300 mg, about 200 to about 300 mg, about 400 to about 600 mg, about 450 to about 550 mg, about 900 to about 1100 mg, about 950 to about 1150 mg, about 1800 to about 2200 mg, about 1900 to about 2100 mg of berberine, or a pharmaceutically acceptable salt thereof. In some embodiments, the composition comprises about 250, about 500, about 750, or about 1000 mg of berberine, or a pharmaceutically acceptable salt thereof. In some embodiments, a specified amount of berberine, or a pharmaceutically acceptable salt thereof, is combined with the other specified amounts of the individual components described herein. In some embodiments, the berberine or the pharmaceutically acceptable salt thereof is complexed with a phospholipid. In some embodiments, the phospholipid is phosphatidylcholine.

Silymarin and silibinin (also known as silybin) is isolated from the milk thistle (*Silybum marianum*) and possesses pharmacological effects such as hepatoprotection, anti-inflammatory and antioxidant actions. Silibinin is the major active constituent of silymarin, a standardized extract of milk thistle seeds, containing a mixture of flavonolignans such as silibinin, isosilibinin, silicristin, silidianin and others. In some embodiments, silibinin is complexed with phospholipids, a formulation which is sold under the trademark Siliphos® (Indena S.p.A.). Siliphos® uses Phytosome®, a proprietary biomimetic strategy for the delivery of natural ingredients. The Phytosome® delivery system combines food-grade sunflower lecithin with botanical and natural substances maintaining the original components' benefits. A Phytosome® is prepared by complexing a polyphenolic phytoconstituent or mixture with a phospholipid (see, e.g., Semalty et al., Fitoterapia 81 (2010) 306-314). In some embodiments, a composition provided herein comprises any of the complexes of phospholipid and either silymarin or silibinin described in U.S. Pat. No. 4,764,508, which is incorporated herein by reference in its entirety.

In some embodiments, the composition comprises about 5 mg to about 1500 mg of silymarin, silibinin, or Siliphos®, or a pharmaceutically acceptable salt thereof, or any combination thereof. In some embodiments, the composition comprises about 5, about 10, about 15, about 20, about 25, about 30, about 35, about 40, about 45, about 50, about 60, about 65, about 70, about 75, about 80, about 90, about 100, about 110, about 120, about 130, about 140, about 150, about 175, about 200, about 250, about 300, about 350, about 400, about 450, about 500, about 600, about 700, about 750, about 800, about 850, about 900, about 950, or about 1500 mg of silymarin, silibinin, or Siliphos®, or a pharmaceutically acceptable salt thereof, or any combination thereof. In some embodiments, the composition comprises about 10 to about 500 mg, about 50 to about 150 mg, about 100 to about 150 mg, about 150 to about 450 mg, about 150 to about 300 mg, about 300 to about 450 mg, about 100 to about 300 mg of silymarin, silibinin, or Siliphos®, or a pharmaceutically acceptable salt thereof, or any combination thereof. In some embodiments, the composition is given twice a day. In some embodiments, the composition comprises about 50, about 100, about 150, about 300, about 450, about 500, about 750, or about 1500 mg of silymarin, silibinin, or Siliphos®, or a pharmaceutically acceptable salt thereof, or any combination thereof. In some embodiments, the specified amount of silymarin, silibinin, or Siliphos®, or a pharmaceutically acceptable salt thereof, or any combination thereof is combined with the other specified amounts of the individual components described herein.

Lipoic acid is an organosulphur compound also known as alpha-lipoic acid or thioctic acid. Lipoic acid is found in yeast, liver, some green vegetables, and potatoes. It has been used as an antioxidant and has been used in diabetics particularly to treat diabetic neuropathy.

In some embodiments, the composition comprises about 100 to about 1000 mg of lipoic acid, or a pharmaceutically acceptable salt thereof. In some embodiments, the composition comprises about 100, about 150, about 200, about 250, about 300, about 350, about 400, about 450, about 500, about 550, about 600, about 650, about 700, about 750, about 800, about 850, about 900, about 950, or about 1000 mg of lipoic acid, or a pharmaceutically acceptable salt thereof. In some embodiments, the composition comprises about 100 to about 200 mg, about 125 to about 175 mg, about 250 to about 500 mg, about 100 to about 750 mg, about 250 to about 350 mg, about 500 to about 700 mg, about 550 to about 650 mg of lipoic acid, or a pharmaceutically acceptable salt thereof. In some embodiments, the composition comprises about 100, about 150, about 200, about 250, about 300, about 350, about 400, about 450, about 500, about 550, about 600 mg of lipoic acid, or a pharmaceutically acceptable salt thereof. In some embodiments, a specified amount of lipoic acid, or a pharmaceutically acceptable salt thereof, is combined with the other specified amounts of the individual components described herein.

Taurine (also known as 2-aminoethanesulfonic acid) is a naturally occurring compound widely distributed in animal tissues. Taurine has been implicated in a range of physiological functions including neurotransmission, protection from excitotoxicity and improvements in cardiovascular and metabolic health.

In some embodiments, the composition comprises about 100 mg to about 2000 mg of taurine, or a pharmaceutically acceptable salt thereof. In some embodiments, the composition comprises about 100, about 150, about 200, about 250, about 300, about 350, about 400, about 450, about 500, about 550, about 600, about 650, about 700, about 750, about 800, about 850, about 900, about 950, about 1000, about 1100, about 1200, about 1300, about 1400, about 1500, about 1600, about 1700, about 1800, about 1900, or about 2000 mg of taurine, or a pharmaceutically acceptable salt thereof. In some embodiments, the composition comprises about 200 to about 1700 mg, about 200 to about 1500 mg, about 300 to about 1500 mg, about 400 to about 1500 mg, about 500 to about 1500 mg, about 600 to about 1500 mg, about 700 to about 1500 mg, about 750 to about 1500 mg, about 800 to about 1500 mg, about 750 to about 1500 mg, about 1000 to about 1500 mg, about 300 to about 500 mg, about 300 to about 400 mg, about 350 to about 400 mg of taurine, about 500 to about 1000 mg, about 600 to about 1000 mg, about 700 to about 1000 mg, about 800 to about 1000 mg, about 900 to about 1000 mg, about 700 to about 800 mg, about 725 to about 775 mg, about 1300 to about 1600 mg, about 1400 to about 1600 mg, about 1450 to about 1550 mg of taurine, or a pharmaceutically acceptable salt thereof. In some embodiments, the composition is given twice a day. In some embodiments, the composition comprises about 300, about 325, about 350, about 375, about 400, about 700, about 725, about 750, about 775, about 1450, about 1475, about 1500, about 1525, or about 1550 mg of taurine, or a pharmaceutically acceptable salt thereof. In some embodiments, a specified amount of taurine, or a pharmaceutically acceptable salt thereof, is combined with the other specified amounts of the individual components described herein.

Phosphatidylcholine is the most abundant phospholipid in cell membranes. In the liver phosphatidylcholine can regulate lipid deposition. Phosphatidylcholine is also found in mitochondrial membranes and is implicated in efficient energy metabolism. In some embodiments, the phosphatidylcholine, or the pharmaceutically acceptable salt thereof, is in a complex with one or more of: (a) the niacin, or the pharmaceutically acceptable salt thereof; (b) the berberine, or the pharmaceutically acceptable salt thereof; (c) the sylimarin, silibinin, or Siliphos®, or any combination thereof, or the pharmaceutically acceptable salt thereof; (d) the lipoic acid, or the pharmaceutically acceptable salt thereof; and (e) the taurine, or the pharmaceutically acceptable salt thereof. In some embodiments, a composition provided herein comprises any of the complexes of phosphatidylcholine and either silymarin and or silibinin described in U.S. Pat. No. 4,764,508, which is incorporated herein by reference in its entirety.

In some embodiments, the composition comprises about 5 mg to about 1000 mg of phosphatidylcholine or a pharmaceutically acceptable salt thereof, or any combination thereof. In some embodiments, the composition comprises about 5, about 10, about 15, about 20, about 25, about 30, about 35, about 40, about 45, about 50, about 60, about 65, about 70, about 75, about 80, about 90, about 100, about 110, about 120, about 130, about 140, about 150, about 175, about 200, about 250, about 300, about 350, about 400, about 450, about 500, about 600, about 700, about 750, about 800, about 850, about 900, about 950, or about 1000 mg of phosphatidylcholine, or a pharmaceutically acceptable salt thereof, or any combination thereof. In some embodiments, the composition comprises about 10 to about 500 mg, about 50 to about 150 mg, about 100 to about 150 mg, about 150 to about 450 mg, about 150 to about 300 mg, about 300 to about 450 mg, about 100 to about 300 mg of phosphatidylcholine, or a pharmaceutically acceptable salt thereof, or any combination thereof. In some embodiments, the composition is given twice a day. In some embodiments, the composition comprises about 50, about 100, about 150, about 300, about 450, about 500, about 750, or about 1000 mg of phosphatidylcholine, or a pharmaceutically acceptable salt thereof, or any combination thereof. In some embodiments, the specified amount of phosphatidylcholine, or a pharmaceutically acceptable salt thereof, or any combination thereof is combined with the other specified amounts of the individual components described herein.

In some embodiments, a composition comprises the amounts of each component as provided in Tables 1 and 2.

TABLE 1

Exemplary compositions

| | Composition 1 | Composition 2 | Composition 3 | Composition 4 |
|---|---|---|---|---|
| Niacin (Vitamin B3, nicotinic acid, nicotinamide, inositol hexanicotinate, nicotinic riboside, NAD or NADH) | 250 mg | 500 mg | 1000 mg | 2000 mg |
| Berberine | 250 mg | 250 mg | 500 mg | 750 mg |
| Silymarin, Silibinin, or Siliphos ®, or any combination thereof | 150 mg | 150 mg | 300 mg | 450 mg |
| Lipoic Acid | 150 mg | 150 mg | 300 mg | 600 mg |
| Taurine | 375 mg | 375 mg | 750 mg | 1500 mg |
| Phosphatidylcholine | 150 mg | 150 mg | 300 mg | 1000 mg |

TABLE 2

Exemplary compositions

| | Composition 5 | Composition 6 | Composition 7 | Composition 8 |
|---|---|---|---|---|
| Niacin (Vitamin B3, nicotinic acid, nicotinamide, inositol hexanicotinate, nicotinic riboside, NAD or NADH) | 250 mg | 500 mg | 1000 mg | 2000 mg |
| Berberine | 250 mg | 250 mg | 500 mg | 1000 mg |
| Silymarin, Silibinin, or Siliphos ®, or any combination thereof | 50 mg | 50 mg | 100 mg | 1100 mg |
| Lipoic Acid | 150 mg | 150 mg | 300 mg | 1500 mg |
| Taurine | 375 mg | 375 mg | 750 mg | 1500 mg |
| Phosphatidylcholine | 50 mg | 50 mg | 500 mg | 750 mg |

In some embodiments, a composition comprises niacin (e.g., vitamin B3, nicotinic acid, nicotinamide, inositol hexanicotinate, nicotinic riboside, NAD or NADH), or a pharmaceutically acceptable salt thereof, in an amount from about 20% to about 40% by weight. In some embodiments, a composition comprises taurine, or the pharmaceutically acceptable salt thereof, in an amount from about 25% to about 35% by weight. In some embodiments, a composition comprises berberine, or the pharmaceutically acceptable salt thereof, in an amount from about 15% to about 20% by weight. In some embodiments, a composition comprises lipoic acid, or the pharmaceutically acceptable salt thereof, in an amount from about 10% to about 15% by weight.

In some embodiments, a composition comprises silymarin, or a pharmaceutically acceptable salt thereof, in an amount from about 8% to about 15% by weight. In some embodiments, a composition comprises silibinin, or a pharmaceutically acceptable salt thereof, in an amount from about 8% to about 15% by weight. In some embodiments, a composition comprises Siliphos®, or a pharmaceutically acceptable salt thereof, in an amount from about 8% to about 15% by weight.

In some embodiments, a composition comprises (i) silymarin, or a pharmaceutically acceptable salt thereof, and (ii) silibinin, or a pharmaceutically acceptable salt thereof, combined, in an amount from about 8% to about 15% by weight.

In some embodiments, a composition comprises (i) silymarin, or a pharmaceutically acceptable salt thereof, and (ii) Siliphos®, or a pharmaceutically acceptable salt thereof, combined, in an amount from about 8% to about 15% by weight. In some embodiments, a composition comprises (i) silibinin, or a pharmaceutically acceptable salt thereof, and (ii) Siliphos®, or a pharmaceutically acceptable salt thereof, combined, in an amount from about 8% to about 15% by weight. In some embodiments, a composition comprises (i) silymarin, or a pharmaceutically acceptable salt thereof, (ii) silibinin, or a pharmaceutically acceptable salt thereof, and (iii) Siliphos®, or a pharmaceutically acceptable salt thereof, combined, in an amount from about 8% to about 15% by weight.

In some embodiments, a composition comprises the five components as provided in Tables 3 and 4.

TABLE 3

Exemplary compositions

| | Composition 9 | Composition 10 | Composition 11 | Composition 12 |
|---|---|---|---|---|
| Niacin (Vitamin B3, nicotinic acid, nicotinamide, inositol hexanicotinate, nicotinic riboside, NAD or NADH) | 21% | 35% | 35% | 32% |
| Berberine | 21% | 17% | 17% | 16% |
| Silymarin, Silibinin, or Siliphos ®, or any combination thereof | 12% | 10% | 10% | 18% |
| Lipoic Acid | 12% | 10% | 10% | 11% |
| Taurine | 31% | 26% | 26% | 24% |
| Phosphatidylcholine | 12% | 10% | 10% | 18% |

TABLE 4

Exemplary compositions

| | Composition 13 | Composition 14 | Composition 15 | Composition 16 |
|---|---|---|---|---|
| Niacin (Vitamin B3, nicotinic acid, nicotinamide, inositol hexanicotinate, nicotinic riboside, NAD or NADH) | 23% | 37% | 37% | 40% |
| Berberine | 23% | 18 | 18% | 15% |
| Silymarin, Silibinin, or Siliphos ®, or any combination thereof | 4.65% | 3% | 3% | 3% |
| Lipoic Acid | 13% | 11% | 11% | 12% |
| Taurine | 34% | 28% | 28% | 30% |
| Phosphatidylcholine | 4% | 3% | 3% | 3% |

In some embodiments, a composition may comprise additional components in addition to the five components listed in the tables. The percentages of each of the five components relative to the whole composition may decrease, but the ratios of the five components relative to each other would remain the same.

Provided herein is a composition comprising: (a) about 250 mg niacin, or a pharmaceutically acceptable salt thereof; about 250 mg berberine, or a pharmaceutically acceptable salt thereof; about 150 mg silymarin, silibinin, or Siliphos®, or any combination thereof, or a pharmaceutically acceptable salt thereof; about 150 mg lipoic acid, or a pharmaceutically acceptable salt thereof; and about 375 mg taurine, or a pharmaceutically acceptable salt thereof; (b) about 500 mg niacin, or a pharmaceutically acceptable salt thereof; about 250 mg berberine, or a pharmaceutically acceptable salt thereof; about 150 mg silymarin, silibinin, or Siliphos®, or any combination thereof, or a pharmaceutically acceptable salt thereof; about 150 mg lipoic acid, or a pharmaceutically acceptable salt thereof; and about 375 mg taurine, or a pharmaceutically acceptable salt thereof; (c) about 1000 mg niacin, or a pharmaceutically acceptable salt thereof; about 500 mg berberine, or a pharmaceutically acceptable salt thereof; about 300 mg silymarin, silibinin, or Siliphos®, or any combination thereof, or a pharmaceutically acceptable salt thereof; about 300 mg lipoic acid, or a pharmaceutically acceptable salt thereof; and about 750 mg taurine, or a pharmaceutically acceptable salt thereof; or (d) about 2000 mg niacin, or a pharmaceutically acceptable salt thereof; about 750 mg berberine, or a pharmaceutically acceptable salt thereof; about 450 mg silymarin, silibinin, or Siliphos®, or any combination thereof, or a pharmaceutically acceptable salt thereof; about 600 mg lipoic acid, or a pharmaceutically acceptable salt thereof; and about 1500 mg taurine, or a pharmaceutically acceptable salt thereof.

In some embodiments, % w/w refers to the mass of the active ingredients. In some embodiments, % w/w refers to the total mass of all ingredients present in a composition.

In some embodiments, the % w/w does not include the weight of the capsule. In some embodiments, the % w/w includes the weight of the capsule. In some embodiments, the % w/w refers to the active ingredients or the five components listed in the tables above.

In some embodiments, the silibinin in the composition is complexed with a phospholipid. In some embodiments, the phospholipid is phosphatidylcholine.

In some embodiments, the berberine in the composition is complexed with a phospholipid. In some embodiments, the phospholipid is a Phytosome.

In some embodiments, a pharmaceutically acceptable salt of a compound (such as niacin (e.g., vitamin B3, nicotinic acid, nicotinamide, inositol hexanicotinate, nicotinic riboside, NAD or NADH), berberine, silymarin or silibinin or Siliphos®, or any combination thereof, lipoic acid, taurine) is a sodium salt, a disodium salt or a potassium salt.

As used herein, the terms and phrases "foodstuff," "food supplement," "beverage," and "beverage supplement" have the normal meanings for those terms and are not restricted to pharmaceutical or nutraceutical preparations. A beverage or foodstuff is something that is suitable for mammal consumption. In some embodiments, the beverage or foodstuff is suitable for human consumption. A composition that is suitable for mammal or human consumption is something that can be ingested without causing harm to the mammal or human. Examples of mammals include, but are not limited to, human, cat, dog, pig, cow, horse, sheep, rodent, rat, mouse, domesticated mammals, and the like. In some embodiments, the foodstuff is a bar. In some embodiments, the beverage is a shake. The beverage can also be in the form of a slurry where the beverage is a mix of liquid and solid. In some embodiments the foodstuff, foodstuff supplement, beverage, or beverage supplement is frozen. In some embodiments, the foodstuff, foodstuff supplement, beverage, or beverage supplement is not frozen. Other composition forms are also included within the present embodiments. These may, for example, include pure or substantially pure compounds such as a foodstuff precursor (such as a rehydratable powder), or a beverage precursor (such as a powder dispersible in water, milk, or other liquid).

In some embodiments, a composition is a solid form preparation. In some embodiments, the solid form preparation is intended to be converted, shortly before use, to liquid form preparations for oral administration to a mammal. Such liquid form preparations include solutions, suspensions, and emulsions. These solid form preparations can be provided in a unit dose form. The unit dose form can provide convenience to the user. The unit dose form can be used to provide a single liquid dosage unit. Alternately, sufficient solid form preparations may be provided so that after conversion to liquid form, multiple individual liquid doses may be obtained by measuring predetermined volumes of the liquid form preparation as with a syringe, teaspoon, or other volumetric container or apparatus. In some embodiments, when multiple liquid doses are so prepared, the unused portion of the liquid doses can be kept at low temperature (i.e., under refrigeration) to, for example, maintain stability. The solid form preparations can also be encapsulated or prepared as a tablet. In some embodiments, the composition is not a liquid or is not intended to be converted, shortly before use, to liquid form preparations for oral administration to a mammal.

In some embodiments, a composition further comprises a pharmaceutically acceptable carrier, diluent, excipient, glidant or flavoring. In some embodiments, a composition may further comprise one or more of: flavoring agent(s), flavor modifier(s), flavor enhancer(s), colorant(s), stabilizer(s), buffer(s), artificial and/or natural sweetener(s), dispersant(s), thickener(s), solubilizing agent(s), and the like. Liquids utilized for preparing the liquid form preparation may be for example, water, fruit juice, vegetable juice, milk, alcohol, and the like, or any mixture thereof.

As used herein, a "flavor" refers to the perception of taste and/or smell in an animal, such as a mammal, which include sweet, sour, salty, bitter, umami, and others. The animal may be a human.

As used herein, a "flavoring agent" refers to a compound, or a biologically acceptable salt thereof, that induces a flavor or taste in a mammal or a human.

As used herein, a "flavor modifier" refers to a compound, or biologically acceptable salt thereof, that modulates, including enhancing or potentiating, and inducing, a taste and/or smell of a natural or synthetic flavoring agent in a mammal or a human.

As used herein, a "flavor enhancer" refers to a compound, or biologically acceptable salt thereof, that enhances a taste or smell of a natural or synthetic flavoring agent. In some embodiments, the flavoring agent is a "savory flavor," which refers to the savory "umami" taste typically induced by MSG (mono sodium glutamate) in a mammal or a human.

Other examples of flavoring agents include, but are not limited to, "sweet flavoring agent," "sweet compound," or "sweet receptor activating compound," which herein refer to a compound, or biologically acceptable salt thereof, that elicits a detectable sweet flavor in a mammal, e.g., sucrose, fructose, glucose, and other known natural saccharide-based sweeteners, or known artificial sweeteners including, but not limited to, sucralose, saccharin, cyclamate, and aspartame. A sweet flavoring agent can also be referred to as a sweetener.

In some embodiments, a composition (e.g., foodstuff or beverage) may further comprise a flavoring agent such as, for example, chocolate fudge, chocolate, vanilla, strawberry, prairie berry, mocha, latte, peach, almond, coconut, raspberry, saskatoon berry, plains berry, apple, orange, butterscotch, coffee, blueberry, bubble gum, cola, root beer, guarana and/or any mixture thereof. In some embodiments, flavoring agents and/or any mixture thereof chosen from the list above can be added from about 0.01 g to about 50 g per 354 ml of a beverage solution.

In some embodiments, a composition further comprises a preservative. The preservative used can be natural and bacteriostatic. In some embodiments, the preservative is benzoic acid and/or a benzoate compound such as, but not limited to, sodium benzoate, potassium lactate, calcium benzoate and/or magnesium benzoate. In some embodiments, a composition comprises from about 0.15 g to about 0.70 g of preservative, such as benzoic acid, sodium benzoate, potassium benzoate, calcium benzoate, magnesium benzoate and/or any mixture thereof.

In some embodiments, a beverage composition may further comprise the addition of carbonation, i.e., the forceful introduction of carbon dioxide gas, under pressure, against a liquid surface, which causes the absorption of the gas into, and in the case of the present compositions, solubilization by the liquid. In some embodiments, from about 0.10 volume to about 4 volumes of gas of the beverage solution. The higher the gas pressure and the cooler the liquid, the more carbonation that is dissolved. Carbonation can, for example, enhance the flavor, sweetness, taste, mouth-feel and/or lowering the pH of the beverage. Carbonation can also change the viscosity to render the beverage more desirable.

In some embodiments, a composition further comprises water, fructose, natural flavors, citric acid, stevia extract, guar gum, xanthan gum, sodium benzoate, potassium sorbate, or a combination thereof. In some embodiments, the guar gum and the xanthan gum are pre-combined.

In some embodiments, a composition further comprises from about 100 to about 200 mg of natural flavors. The natural flavors can be any natural flavors. In some embodiments, a composition comprises from about 0.2 to about 0.3% w/w of natural flavors.

In some embodiments, a composition further comprises stevia extract. In some embodiments, the composition comprises about 1-100, 1-90, 1-80, 1-70, 1-60, 1-50, 1-40, 1-30, 1-20, 20-40, 30-40, or 35-40 mg of stevia extract. In some embodiments, a composition comprises about 0.06-0.07% w/w of stevia extract.

In some embodiments, additional ingredients can be added to a composition, and the remaining weight can be filled by water. For example, in some embodiments, the composition comprises about 90-99, 90-98, 90-97, 90-96, 90-95, 90-94, or 93-94% w/w of water. In some embodiments, the composition comprises at least 90, 91, 92, 93, 94, 95, 96, 97, 98, 99, or 99.9% w/w of water.

In some embodiments, a composition is gluten free. In some embodiments, a composition is free of artificial or synthetic preservatives.

In some embodiments, a composition can be prepared by mixing the components together. In some embodiments, the powder is mixed with a saline solution. In some embodiments, the composition comprises magnesium sulfate, a detergent or nonionic surfactant, such as Tween® 20 (polysorbate 20), a polyethylene glycol (e.g., PEG400), and the like.

In some embodiments, a composition described herein can be in the form of a powder. This powder can be a powdered beverage mix that can be added to a liquid to make a beverage. The powder can also be mixed with other powdered beverage mixes. In some embodiments, the powder is encapsulated (e.g., in a capsule). In some embodiments, a composition described herein can be a beverage. In some embodiments, the beverage is a 2-ounce beverage, a 4-ounce beverage, or a beverage from 2 ounces to 4 ounces. The beverage can then be consumed by a mammal. In addition to the liquids described herein, the liquid can also be characterized as an aqueous solution. In some embodiments, the aqueous solution is free of alcohol and/or organic solvents. In some embodiments, the solution is free of methanol, isopropanol, ethanol, and/or butanol. In some embodiments a liquid comprising a composition is lyophilized to form a powder.

In some embodiments, a composition described herein can be a beverage. The beverage can be placed in various beverage containers. Examples of beverage containers include, but are not limited to, can(s), bottle(s), and pouch(es). Additional examples of beverage containers include those types of containers suitable for dispensing soda, including, for example, kegs. The beverage container can be made of any suitable material such as, but not limited to, glass, plastic, aluminum, or aluminum-coated plastic and the like. In some embodiments, the pouch is a plastic pouch or an aluminum foil pouch. The compositions can also be a powder that can be dissolved in a liquid. The powder can also be contained in a container or a beverage container. The container can be any suitable material such as glass, plastic, or metal (e.g., aluminum). The container can then be opened, and the contents can be contacted (e.g., poured) into the liquid. In some embodiments a liquid is added to a container comprising one or more compositions described herein.

The compositions described herein can be delivered by any suitable method, e.g., topically, orally or parenterally. In some embodiments, the delivery form is liquid or a solid such as a powder that can be stirred into an ingestible liquid. The compositions can also be delivered as a tablet, pill, capsule, gummy and the like. Standard pharmaceutical carriers for topical, oral, or parenteral compositions may be used, many of which are described in Remington's Pharmaceutical Sciences, Mack Publishing Co., Easton, Pa.

For example, for oral administration, suitable pharmaceutical carriers or diluents can include mannitol, lactose, starch, magnesium stearate, talcum, glucose, and magnesium carbonate. Oral compositions can be in the form of tablets, capsules, powders, solutions, suspensions, sustained release formulations, and the like. A typical tablet or capsule can contain lactose, 1-2% magnesium stearate, and 10-20% cornstarch, along with the active substance (e.g., about 0.001-20%).

For parenteral administration, suitable pharmaceutical carriers can include water, saline, dextrose, Hank's solution, Ringer's solution, glycerol, and the like. Parenteral compositions can be in the form of suspensions, solutions, emulsions, and the like.

Parenteral administration is usually by injection or infusion which can be subcutaneous, intramuscular, or intravenous.

Methods of Producing Compositions

The compositions described herein can be made according to any mixing protocol or method of manufacture. In some embodiments, the raw materials are mixed and placed in a capsule or formed into a tablet. In some embodiments, the raw materials are prepared as a blend and then dissolved in water simultaneously. In some embodiments, the solution is filtered to remove any non-dissolved material. In some embodiments, each ingredient is added sequentially to the water. In some embodiments, the aqueous composition is heat pasteurized. In some embodiments, the composition is aliquoted into dosage forms. In some embodiments, a dosage form is a 2 liquid ounce form, a 3 liquid ounce form, or a 4 liquid ounce form. In some embodiments, the composition is not heat pasteurized, and a bottle or package is cold filled with the aqueous composition.

Methods of Using Compositions

Further provided herein are methods of using the compositions described herein (i.e., compositions comprising (1) silymarin, silibinin, or Siliphos®, or any combination thereof, (2) niacin (vitamin B3, nicotinic acid, nicotinamide, inositol hexanicotinate, nicotinic riboside, NAD or NADH), (3) taurine, (4) berberine, (5) lipoic acid, and phosphatidyl choline or pharmaceutically acceptable salts of any of the preceding. For example, the compositions may be used to treat or prevent neurodegeneration, NASH, NAFL, hepatic-dysfunction and metabolic-related disorders including obesity.

The apolipoprotein E (APOE) gene alleles present in a subject can determine the subject's responsiveness or level of responsiveness to the compositions provided herein. ApoE (the protein encoded by APOE) associates with lipid particles and mainly functions in lipoprotein-mediated lipid transport between organs via the plasma and interstitial fluids. There are three major APOE alleles in humans: F2 or APOE2 (frequency ~6%), F3 or APOE3 (frequency ~78%), and F4 or APOE4 (frequency ~15%). Provided herein are methods for using the APOE allele genotype of a subject as a prognostic marker to predict responsiveness to treatment by a composition provided herein. Provided herein is a method for determining the responsiveness of a subject to a composition provided herein, the method comprising determining the genotype of the APOE isoform in the subject. In some embodiments, the presence of one or two APOE3 alleles in the subject's genotype determines that the subject will be responsive to the composition. In some embodiments, the presence of one or two APOE4 alleles in the subject's genotype determines that the subject will be responsive to the composition. In some embodiments, the presence of one or two APOE3 alleles in the subject's genotype determines that the subject will be more responsive to the composition than a subject having one or two APOE4 alleles or a subject having one or two APOE2 alleles.

In some embodiments, a method provided herein further comprises determining the genotype of the APOE isoform in the subject before administering the composition to the subject. In some embodiments, the subject administered an effective amount of a composition described herein has one or two APOE4 alleles. In some embodiments, the subject administered an effective amount of a composition described herein has one or two APOE3 alleles. In some embodiments, the subject administered an effective amount of a composition described herein has one or two APOE2 alleles. In some embodiments, a method provided herein further comprises determining that the subject has one or two APOE4 alleles before administering the composition to the subject. In some embodiments, a method provided herein further comprises determining that the subject has one or two APOE3 alleles before administering the composition to the subject.

Provided herein is a method for conferring neuroprotection on a subject in need thereof, the method comprising administering to the subject an effective amount of a composition described herein. In some embodiments, the neuroprotection comprises a reduction or a slowing of a functional decline. In some embodiments, the subject has a neurodegenerative condition. In some embodiments, the functional decline is associated with the neurodegenerative condition. In some embodiments, the subject has Alzheimer's disease, dementia, senile systemic amyloidosis, amyloidosis, cerebrovascular amyloidosis or cerebral amyloid angiopathy. Provided herein is a method for conferring neuroprotection on a subject in need thereof, the method comprising (i) determining that the subject has one or two APOE3 alleles; and (ii) administering to the subject an effective amount of a composition described herein. Provided herein is a method for conferring neuroprotection on a subject in need thereof, the method comprising (i) determining that the subject has one or two APOE4 alleles; and (ii) administering to the subject an effective amount of a composition described herein.

Also provided herein is a method for treating or preventing dementia in a subject in need thereof, the method comprising administering to the subject an effective amount of a composition described herein. Provided herein is a method for treating or preventing dementia in a subject in need thereof, the method comprising (i) determining that the subject has one or two APOE3 alleles; and (ii) administering to the subject an effective amount of a composition described herein. Provided herein is a method for treating or preventing dementia in a subject in need thereof, the method comprising (i) determining that the subject has one or two APOE4 alleles; and (ii) administering to the subject an effective amount of a composition described herein. Further provided herein is a method for treating or preventing neurodegeneration in a subject in need thereof, the method comprising administering to the subject an effective amount of a composition described herein. Provided herein is a method for treating or preventing neurodegeneration in a subject in need thereof, the method comprising (i) determining that the subject has one or two APOE3 alleles; and (ii) administering to the subject an effective amount of a composition described herein. Provided herein is a method for treating or preventing neurodegeneration in a subject in need thereof, the method comprising (i) determining that the subject has one or two APOE4 alleles; and (ii) administering to the subject an effective amount of a composition described herein.

Also provided herein is a method for reducing brain β-amyloid levels in a subject in need thereof, the method comprising administering to the subject an effective amount of a composition described herein. In some embodiments, the amyloid is Aβ40 or Aβ42, or any combination thereof. Provided herein is a method for reducing brain amyloid beta levels in a subject in need thereof, the method comprising (i) determining that the subject has one or two APOE3 alleles; and (ii) administering to the subject an effective amount of a composition described herein. Provided herein is a method for reducing brain amyloid beta levels in a subject in need thereof, the method comprising (i) determining that the subject has one or two APOE4 alleles; and (ii) administering to the subject an effective amount of a composition described herein. Provided herein is a method for reducing the accumulation of an amyloid peptide in a subject in need thereof, the method comprising administering to the subject an effective amount of a composition described herein. Provided herein is a method for reducing the accumulation of an amyloid peptide in a subject in need thereof, the method comprising (i) determining that the subject has one or two APOE3 alleles; and (ii) administering to the subject an effective amount of a composition described herein. Provided herein is a method for reducing the accumulation of an amyloid peptide in a subject in need thereof, the method comprising (i) determining that the subject has one or two APOE4 alleles; and (ii) administering to the subject an effective amount of a composition described herein.

Provided herein is a method for treating or preventing Alzheimer's disease (AD) in a subject in need thereof, the method comprising administering to the subject an effective amount of a composition described herein. Provided herein is a method for treating or preventing a symptom of AD in a subject in need thereof, the method comprising administering to the subject an effective amount of a composition described herein. In some embodiments, the symptom of AD is a memory defect.

APOE is the primary genetic factor associated with late-onset AD, which comprises most AD cases. The major APOE alleles in humans are associated with AD risk as follows: ε2 or APOE2 (associated with decreased risk for AD), ε3 or APOE3 (neutral risk), and ε4 or APOE4 (increased risk). The effect of the apolipoprotein ε4 allele (APOE4) on disease status is dramatic, with APOE4 homozygotes having up to 15 times, and APOE4 heterozygotes up to 4 times, the risk for AD when compared to risk neutral APOE3 homozygotes. Despite this influence, the role of APOE, which encodes apolipoprotein E (ApoE), in AD remains incompletely understood, although there is much evidence that it is pleiotropic and may exert an influence in AD pathophysiology via effects on metabolism, synaptic function, neurodevelopment, inflammation, and amyloid-β (Aβ) aggregation and clearance.

In some embodiments, a method for preventing or treating AD (or a symptom of AD) in a subject in need thereof further comprises determining the genotype of the APOE isoform in the subject. In some embodiments, the genotype of the APOE isoform in the subject is determined before a composition described herein is administered to the subject to treat, e.g., AD or a symptom of AD. Provided herein is a method for treating or preventing AD in a subject in need thereof, the method comprising (i) determining that the subject has one or two APOE4 alleles; and (ii) administering to the subject an effective amount of a composition described herein. Provided herein is a method for treating or preventing AD in a subject in need thereof, the method comprising (i) determining that the subject has one or two APOE3 alleles; and (ii) administering to the subject an effective amount of a composition described herein.

In some embodiments, administration of an effective amount of a composition described herein i) reduces the occurrence, (ii) increases the age of onset, (iii) slows the rate of progression of amyloid accumulation, Provided herein is a method for supporting or maintaining a healthy memory in a subject in need thereof, the method comprising administering to the subject an effective amount of a composition described herein. In some embodiments, the subject is pre-symptomatic. Provided herein is a method for supporting or maintaining a healthy memory in a subject in need thereof, the method comprising (i) determining that the subject has one or two APOE3 alleles; and (ii) administering to the subject an effective amount of a composition described herein. Provided herein is a method for supporting or maintaining a healthy memory in a subject in need thereof, the method comprising (i) determining that the subject has one or two APOE4 alleles; and (ii) administering to the subject an effective amount of a composition described herein. In some embodiments, the subject has a symptom of a memory defect. In some embodiments, the memory defect is a short-term memory defect. Provided herein is a method for treating or preventing a short-term memory defect in a subject in need thereof, the method comprising administering to the subject an effective amount of a composition described herein.

Further provided herein is a method for preventing or treating obesity in a subject in need thereof, the method comprising administering to the subject an effective amount of a composition described herein. Provided herein is a method for preventing or treating obesity in a subject in need thereof, the method comprising (i) determining that the subject has one or two APOE3 alleles; and (ii) administering to the subject an effective amount of a composition described herein. Provided herein is a method for preventing or treating obesity in a subject in need thereof, the method comprising (i) determining that the subject has one or two APOE4 alleles; and (ii) administering to the subject an effective amount of a composition described herein. Provided herein is a method for reducing weight gain in a subject in need thereof, the method comprising administering to the subject an effective amount of a composition described herein. Provided herein is a method for reducing weight gain in a subject in need thereof, the method comprising (i) determining that the subject has one or two APOE3 alleles; and (ii) administering to the subject an effective amount of a composition described herein. Provided herein is a method for reducing weight gain in a subject in need thereof, the method comprising (i) determining that the subject has one or two APOE4 alleles; and (ii) administering to the subject an effective amount of a composition described herein. In some embodiments, an effective amount of a composition described herein may be administered to companion animals, for example, for preventing or treating metabolic dysfunction, hepatic dysfunction or obesity or for reducing weight gain in the animal. In some embodiments, a companion animal is a cat or a dog.

Provided herein is a method for preventing or treating metabolic syndrome in a subject in need thereof, the method comprising administering to the subject an effective amount of a composition described herein. Provided herein is a method for preventing or treating metabolic syndrome in a subject in need thereof, the method comprising (i) determining that the subject has one or two APOE3 alleles; and (ii) administering to the subject an effective amount of a composition described herein. Provided herein is a method for preventing or treating metabolic syndrome in a subject in need thereof, the method comprising (i) determining that the subject has one or two APOE4 alleles; and (ii) administering to the subject an effective amount of a composition described herein. Provided herein is a method for preventing or treating a symptom of metabolic syndrome in a subject in need thereof, the method comprising administering to the subject an effective amount of a composition described herein. In some embodiments, the symptom of metabolic syndrome is a liver change, insulin sensitivity, glucose sensitivity or lipid regulation. In some embodiments, a symptom of metabolic syndrome is hyperlipidemia.

Non-alcoholic fatty liver disease (NAFLD) is a complex spectrum of liver diseases with risk factors almost identical to those of metabolic syndrome, for example, obesity, diabetes, hyperlipidemia and hypertension. An initial accumulation of lipid in the liver results in simple hepatic steatosis, a relatively benign condition. However, if lipids continue to accumulate and the liver becomes inflamed the disease can progress into non-alcoholic steatohepatitis (NASH) and fibrosis which can lead to more serious health issues; cirrhosis, hepatocellular carcinoma (HCC) and ultimately end-stage liver disease. Because of the propensity for NASH and fibrosis to progress to end-stage liver disease, with few treatment options available, there is a high level of need to identify and produce drug therapies to correct the underlying metabolic deficits, and to prevent or alleviate hepatic fibrosis and NASH.

Provided herein is a method for preventing or treating hyperlipidemia in a subject in need thereof, the method comprising administering to the subject an effective amount of a composition described herein. Provided herein is a method for preventing or treating hyperlipidemia in a subject in need thereof, the method comprising (i) determining that the subject has one or two APOE3 alleles; and (ii) administering to the subject an effective amount of a composition described herein. Provided herein is a method for preventing or treating hyperlipidemia in a subject in need thereof, the method comprising (i) determining that the subject has one or two APOE4 alleles; and (ii) administering to the subject an effective amount of a composition described herein. Provided herein is a method for treating or preventing NAFLD in a subject in need thereof, the method comprising administering to the subject an effective amount of a composition described herein. Provided herein is a method for preventing or treating NAFLD in a subject in need thereof, the method comprising (i) determining that the subject has one or two APOE3 alleles; and (ii) administering to the subject an effective amount of a composition described herein. Provided herein is a method for preventing or treating NAFLD in a subject in need thereof, the method comprising (i) determining that the subject has one or two APOE4 alleles; and (ii) administering to the subject an effective amount of a composition described herein. Provided herein is a method for treating or preventing NASH in a subject in need thereof, the method comprising administering to the subject an effective amount of a composition described herein. Provided herein is a method preventing or treating NASH in a subject in need thereof, the method comprising (i) determining that the subject has one or two APOE3 alleles; and (ii) administering to the subject an effective amount of a composition described herein. Provided herein is a method preventing or treating NASH in a subject in need thereof, the method comprising (i) determining that the subject has one or two APOE4 alleles; and (ii) administering to the subject an effective amount of a composition described herein. Provided herein is a method for treating or preventing liver-related disorders in a subject in need thereof, the method comprising administering to the subject an effective amount of a composition described herein. Provided herein is a method for preventing or treating liver-related disorders in a subject in need thereof, the method comprising (i) determining that the subject has one or two APOE3 alleles; and (ii) administering to the subject an effective amount of a composition described herein. Provided herein is a method for preventing or treating liver-related disorders in a subject in need thereof, the method comprising (i) determining that the subject has one or two APOE4 alleles; and (ii) administering to the subject an effective amount of a composition described herein. Provided herein is a method for preventing or treating fatty liver, protecting liver function, or ameliorating liver disease caused by fatty liver in a subject in need thereof, the method comprising administering to the subject an effective amount of a composition described herein. Provided herein is a method for preventing or treating fatty liver, protecting liver function, or ameliorating liver disease caused by fatty liver in a subject in need thereof, the method comprising (i) determining that the subject has one or two APOE3 alleles; and (ii) administering to the subject an effective amount of a composition described herein. Provided herein is a method for preventing or treating fatty liver, protecting liver function, or ameliorating liver disease caused by fatty liver in a subject in need thereof, the method comprising (i) determining that the subject has one or two APOE4 alleles; and (ii) administering to the subject an effective amount of a composition described herein.

Provided herein is a method for preventing or treating mitochondrial dysfunction in a subject in need thereof, the method comprising administering to the subject an effective amount of a composition described herein. Provided herein is a method for preventing or treating a disease of mitochondrial dysfunction in a subject in need thereof, the method comprising administering to the subject an effective amount of a composition described herein. In some embodiments, a disease of mitochondrial dysfunction is Parkinson's disease. Provided herein is a method for preventing or treating mitochondrial dysfunction in a subject in need thereof, the method comprising (i) determining that the subject has one or two APOE3 alleles; and (ii) administering to the subject an effective amount of a composition described herein. Provided herein is a method for preventing or treating mitochondrial dysfunction in a subject in need thereof, the method comprising (i) determining that the subject has one or two APOE4 alleles; and (ii) administering to the subject an effective amount of a composition described herein.

Also provided herein is a method for enhancing the efficacy of an anti-obesity agent (or an anti-obesity therapy) in a subject in need thereof, the method comprising administering to the subject the anti-obesity agent and an effective amount of a composition described herein. In some embodiments, an anti-obesity agent is a GLP-1 agonist, a 5-HT2c agonist, or a combination of agents.

Further provided herein is a method of administering an anti-obesity agent and an effective amount of the composition of a composition described herein to a subject in need thereof, wherein the dose of the anti-obesity agent is lower than the dose of the anti-obesity agent administered without the effective amount of the composition. In some embodiments, the efficacy of the anti-obesity agent administered with the effective amount of the composition is substantially identical to the efficacy of the anti-obesity agent administered without the effective amount of the composition.

In some embodiments, a method described herein further comprises determining the levels of acylcarnitines and/or branch chain amino fatty acids (BCAA) (e.g., keto acids) in the subject as an indicator of treatment outcome and/or disease status.

Also provided herein is a composition as described herein for use as a medicament.

In some embodiments, a composition is administered orally or by any other route described herein.

In some embodiments, a composition is administered to the subject twice daily, daily, weekly, biweekly, or monthly. In some embodiments, a composition is orally administered to the subject twice daily, daily, weekly, biweekly, or monthly. In some embodiments, a composition is administered to the subject twice a day.

In some embodiments, the subject is a subject in need thereof. As used herein, the phrase "in need thereof" means that the subject, animal or mammal has been identified or suspected as having a need for the particular method or treatment. In some embodiments, the identification can be by any means of diagnosis. In any of the methods and treatments described herein, the animal or mammal can be in need thereof.

As used herein, the term "subject," "individual" or "patient," used interchangeably, means any animal, including mammals, such as mice, rats, other rodents, rabbits, dogs, cats, swine, cattle, sheep, horses, or primates, such as humans or non-human primates.

In some embodiments, the amount is administered in a therapeutically effective amount. As used herein, the phrase "therapeutically effective amount" means the amount of the composition or the individual components that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Amounts can also be determined based on monitoring of the subject's response to treatment.

Amounts of a composition administered to a subject will vary dependent upon the condition, age and weight of the mammal administered the composition, the condition to be treated, supported, or maintained, and the mode of administration.

As used herein, the terms "treat," "treated," or "treating" can refer to therapeutic treatment and/or prophylactic or preventative measures wherein the object is to prevent or slow down (lessen) an undesired physiological condition, disorder or disease, or obtain beneficial or desired clinical results of the conditions or results described herein. For purposes of the embodiments described herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment can also include eliciting a clinically significant response without excessive levels of side effects.

NUMBERED EMBODIMENTS

Notwithstanding the appended claims, the disclosure sets forth the following numbered embodiments:

1. A composition comprising:
   (a) niacin, or a pharmaceutically acceptable salt thereof;
   (b) berberine, or a pharmaceutically acceptable salt thereof;
   (c) sylimarin, silibinin, or Siliphos®, or any combination thereof, or a pharmaceutically acceptable salt thereof;
   (d) lipoic acid, or a pharmaceutically acceptable salt thereof;
   (e) taurine, or a pharmaceutically acceptable salt thereof; and
   (f) phosphatidylcholine or a pharmaceutically acceptable salt thereof.

2. The composition of embodiment 1, wherein the niacin is vitamin B3, nicotinic acid, nicotinamide, inositol hexanicotinate, nicotinic riboside, nicotinamide adenine dinucleotide (NAD) or NADH.

3. The composition of embodiment 1 or 2, wherein the berberine or the pharmaceutically acceptable salt thereof is complexed with a phospholipid.

4. The composition of any one of embodiments 1-3, wherein the phosphatidylcholine, or the pharmaceutically acceptable salt thereof, is in a complex with one or more of:
   (a) the niacin, or the pharmaceutically acceptable salt thereof;
   (b) the berberine, or the pharmaceutically acceptable salt thereof;
   (c) the sylimarin, silibinin, or Siliphos®, or any combination thereof, or the pharmaceutically acceptable salt thereof;
   (d) the lipoic acid, or the pharmaceutically acceptable salt thereof; and
   (e) the taurine, or the pharmaceutically acceptable salt thereof.

5. The composition of any one of embodiments 1-4, wherein the niacin, or the pharmaceutically acceptable salt thereof, is in an amount from about 20% to about 40% by weight.

6. The composition of any one of embodiments 1-5, wherein the berberine, or the pharmaceutically acceptable salt thereof, is in an amount from about 10% to about 20% by weight.

7. The composition of any one of embodiments 1-6, wherein the silymarin, or the pharmaceutically acceptable salt thereof, is in an amount from about 8% to about 20% by weight.

8. The composition of any one of embodiments 1-6, wherein the silibinin, or the pharmaceutically acceptable salt thereof, is in an amount from about 8% to about 20% by weight.

9. The composition of any one of embodiments 1-6, wherein the Siliphos®, or the pharmaceutically acceptable salt thereof, is in an amount from about 8% to about 20% by weight.

10. The composition of any one of embodiments 1-6, wherein the silymarin, or the pharmaceutically acceptable salt thereof, and the silibinin, or the pharmaceutically acceptable salt thereof, combined, are in an amount from about 8% to about 20% by weight.

11. The composition of any one of embodiments 1-6, wherein the silymarin, or the pharmaceutically acceptable salt thereof, and the Siliphos®, or the pharmaceutically acceptable salt thereof, combined, are in an amount from about 8% to about 20% by weight.

12. The composition of any one of embodiments 1-6, wherein the silibinin, or the pharmaceutically acceptable salt thereof, and the Siliphos®, or the pharmaceutically acceptable salt thereof, combined, are in an amount from about 8% to about 20% by weight.

13. The composition of any one of embodiments 1-6, wherein the silymarin, or the pharmaceutically acceptable salt thereof, the silibinin, or the pharmaceutically acceptable salt thereof, and the Siliphos®, or the pharmaceutically acceptable salt thereof, combined, are in an amount from about 8% to about 20% by weight.

14. The composition of any one of embodiments 1-13, wherein the lipoic acid, or the pharmaceutically acceptable salt thereof, is in an amount from about 5% to about 15% by weight.

15. The composition of any one of embodiments 1-14, wherein the taurine, or the pharmaceutically acceptable salt thereof, is in an amount from about 20% to about 35% by weight.

16. The composition of any one of embodiments 1-15, wherein the phosphatidylcholine, or the pharmaceutically acceptable salt thereof, is in an amount from about 5% to about 20% by weight.

17. The composition of any one of embodiments 1-4, wherein the composition comprises:
   (a) about 250 mg niacin, or a pharmaceutically acceptable salt thereof; about 250 mg berberine, or a pharmaceutically acceptable salt thereof; about 150 mg silymarin, silibinin, or Siliphos®, or any combination thereof, or a pharmaceutically acceptable salt thereof; about 150 mg lipoic acid, or a pharmaceutically acceptable salt thereof; and about 375 mg taurine, or a pharmaceutically acceptable salt thereof;
   (b) about 500 mg niacin, or a pharmaceutically acceptable salt thereof; about 250 mg berberine, or a pharmaceutically acceptable salt thereof; about 150 mg silymarin, silibinin, or Siliphos®, or any combination thereof, or a pharmaceutically acceptable salt thereof; about 150 mg lipoic acid, or a pharmaceutically acceptable salt thereof; and about 375 mg taurine, or a pharmaceutically acceptable salt thereof;
   (c) about 1000 mg niacin, or a pharmaceutically acceptable salt thereof; about 500 mg berberine, or a pharmaceutically acceptable salt thereof; about 300 mg silymarin, silibinin, or Siliphos®, or any combination thereof, or a pharmaceutically acceptable salt thereof; about 300 mg lipoic acid, or a pharmaceutically acceptable salt thereof; and about 750 mg taurine, or a pharmaceutically acceptable salt thereof; or
   (d) about 2000 mg niacin, or a pharmaceutically acceptable salt thereof; about 750 mg berberine, or a pharmaceutically acceptable salt thereof; about 450 mg silymarin, silibinin, or Siliphos®, or any combination thereof, or a pharmaceutically acceptable salt thereof; about 600 mg lipoic acid, or a pharmaceutically acceptable salt thereof; and about 1500 mg taurine, or a pharmaceutically acceptable salt thereof.

18. The composition of any one of embodiments 3-17, wherein the phospholipid is phosphatidylcholine.

19. The composition of any one of embodiments 1-18, wherein the composition further comprises a pharmaceutically acceptable carrier, diluent, excipient, or flavoring.

20. A method for preventing or treating obesity in a subject in need thereof, the method comprising administering to the subject an effective amount of the composition of any one of embodiments 1-19.

21. A method for preventing or treating a symptom of metabolic syndrome in a subject in need thereof, the method comprising administering to the subject an effective amount of the composition of any one of embodiments 1-19.

22. The method of embodiment 21, wherein the symptom of metabolic syndrome is a liver change, insulin sensitivity, glucose sensitivity or lipid regulation.

23. A method for preventing or treating non-alcoholic fatty liver disease (NAFLD), non-alcoholic steatohepatitis (NASH) or fatty liver in a subject in need thereof, the method comprising administering to the subject an effective amount of the composition of any one of embodiments 1-19.

24. A method for conferring neuroprotection on a subject in need thereof, the method comprising administering to the subject an effective amount of the composition of any one of embodiments 1-19.

25. The method of embodiment 24, wherein the subject has a neurodegenerative condition, Alzheimer's disease, dementia, senile systemic amyloidosis, amyloidosis, cerebrovascular amyloidosis or cerebral amyloid angiopathy.

26. A method for treating or preventing a disease of mitochondrial dysfunction in a subject in need thereof, the method comprising administering to the subject an effective amount of the composition of any one of embodiments 1-19.

27. The method of embodiment 26, wherein the disease of mitochondrial dysfunction is Parkinson's disease.

28. A method for enhancing the efficacy of an anti-obesity agent in a subject in need thereof, the method comprising administering to the subject the anti-obesity agent and an effective amount of the composition of any one of embodiments 1-19.

29. The method of any one of embodiments 20-28, wherein the method further comprises determining the genotype of the APOE isoform in the subject before administering the composition to the subject.

30. The method of embodiment 29, wherein the subject has
(a) one or two APOE4 alleles;
(b) one or two APOE3 alleles; or
(c) one or two APOE2 alleles.

31. The method of any of the embodiments 20-30, wherein the method further comprises determining the levels of acylcarnitines and/or branch chain amino acids (BCAA) in the subject as an indicator of treatment outcome and/or disease status.

32. The method of any one of embodiments 20-31, wherein the composition is orally administered to the subject twice daily, daily, weekly, biweekly, or monthly.

33. The composition of any one of embodiments 1-19 for use as a medicament.

The present embodiments are now described with reference to the following examples. The examples are provided for the purpose of illustration only and the invention should in no way be construed as being limited to the examples, but rather should be construed to encompass any and all variations which become evident as a result of the teaching provided herein. Those of skill in the art will readily recognize a variety of non-critical parameters that could be changed or modified.

EXAMPLES

Example 1: In Vivo Studies of Effects of an Exemplary Composition

In all studies described below, animals on the test diet received either a high fat diet (HFD) or a low-fat diet (LFD) ad libitum, with the diet further containing the components listed in Table 5.

TABLE 5

| Compound | Source | Single Dose (mg/kg) | Body weight (g) | Food Intake (g) | Daily Dose (mg/kg of HFD diet) | Daily Dose (mg/kg of LFD diet) |
| --- | --- | --- | --- | --- | --- | --- |
| Nicotinic acid | Sigma # N4126-5G | 351 | 25 | 4 | 2193.75 | 1787.0 |
| Berberine | Sigma # B3251-5G | 176 | 25 | 4 | 1100 | 896.3 |
| Siliphos ® | Indena | 200 | 25 | 4 | 1250 | 1017.9 |
| Lipoic acid | Sigma # 62320-5G-F | 105 | 25 | 4 | 656.25 | 534.4 |
| Taurine | Sigma # T0625-10G | 264 | 25 | 4 | 1650 | 1344.1 |

Example 1A: Pharmacokinetic Profile of an Exemplary Composition in Plasma and Brain of Mice Following Administration of a High Fat Diet (HFD) for 10 Days Adult female wild-type C57/BL6 (Envigo) were used for the experiments. The animals were group housed in plastic cages (3-5 animals/cage) and had access to food and water ad libitum. Experiments were approved by the Institutional Animal Care and Use Committee of Brains On-Line LLC, South San Francisco, CA.

Mice were fed a HFD containing a composition comprising nicotinic acid, berberine, silibinin, lipoic acid and taurine (see Table 5) for 10 days. Subjects were euthanized, and plasma and brain samples were collected after 10 days feeding with a HFD containing the composition. The blood was collected into a vial already containing EDTA anticoagulant. The blood was centrifuged at 2500×g at 4° C. for 10 minutes. Supernatants were stored as plasma samples at −80° C. Immediately following blood collection, whole brains were rapidly extracted, placed into a pre-weighed tube, and weighed. Samples were snap frozen with liquid nitrogen.

Levels of nicotinic acid, berberine, silibinin (active form of Siliphos®), lipoic acid and taurine were quantified in plasma and brain samples by LC-MS/MS. All five components were measurable in both plasma and brain following the 10 days administration. Table 6 provides a summary of plasma and brain levels of the components after 10 days administration in an HFD.

TABLE 6

| Ingredient | Basal Plasma | Cumulative Plasma | Basal Brain | Cumulative Brain |
|---|---|---|---|---|
| Nicotinic acid | <LLOQ | 1362 ± 47 nM | 9.4 ± 0.1 nmol/g | 12.6 ± 0.15 nmol/g |
| Berberine | ND | 20.5 ± 16.7 nM | ND | 265 ± 128 pmol/g |
| Silibinin (Siliphos ®) | ND | 21 nM (n = 1) | ND | 12.9 pmol/g (n = 2) |
| Lipoic acid | <LLOQ | 68.2 ± 15.3 nM | <LLOQ | 21 ± 2.4 pmol/g |
| Taurine* | 512 ± 68 µM | 476 ± 12.5 µM | 10 ± 0.36 µmol/g | 8.5 ± 0.9 µmol/g |

*Measure of total plasma and brain taurine
ND = Not detected
<LLOQ = less than lower limits of quantification These data demonstrate that over a 10-day period the combination of ingredients can be detected in both plasma and brain.

Example 1B: Effects of Administration of a High Fat Diet (HFD) Containing an Exemplary Composition on Wild-Type Mice Male wild-type C57BL/6 mice (Jackson Labs) were purchased at 8-10 weeks of age and allowed to acclimate in the animal facility until 12 weeks of age. At this point, mice were randomly divided into one of two groups; 1) control or 2) treatment. All mice were fed a HFD consisting of 45% calories from lard (control diet). The treatment group received the same diet with the addition of the exemplary composition (Table 5). The following parameters were measured:
Body weight
Food intake
Body composition
Blood glucose
Plasma collected for future analysis
Glucose and insulin tolerance testing was conducted at intervals during the study
48 hr. energy expenditure was conducted (CLAMS (Comprehensive Lab Animal Monitoring System))
Feces were collected during the CLAMS experiments
At termination, metabolic tissues were harvested, weighed, and collected for histology (formalin fixed) or frozen for future analysis (gene expression, metabolomics, proteomics) using standard techniques.
Results from this experiment are depicted in FIG. 1, FIG. 3, FIG. 4 and FIG. 5.

Figure 2:
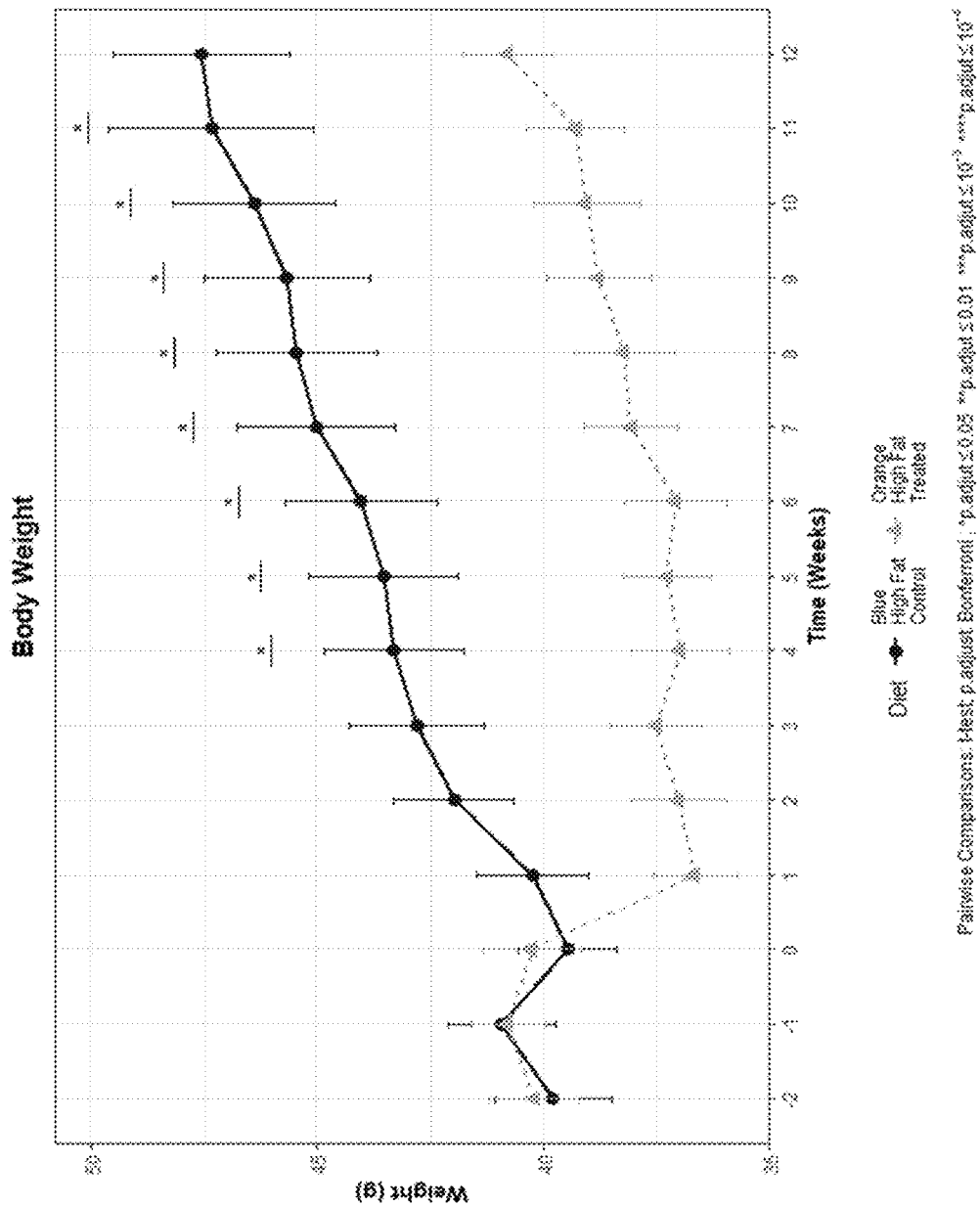
FIG. 2 is a graph depicting the effect of treatment (triangle) on the body weight of wild type (diet-induced obesity) diet-induced obese (DIO) mice maintained on a HFD over a 12-week period. Control (circle) DIO mice were maintained on a HFD but not treated.
Figure 3:
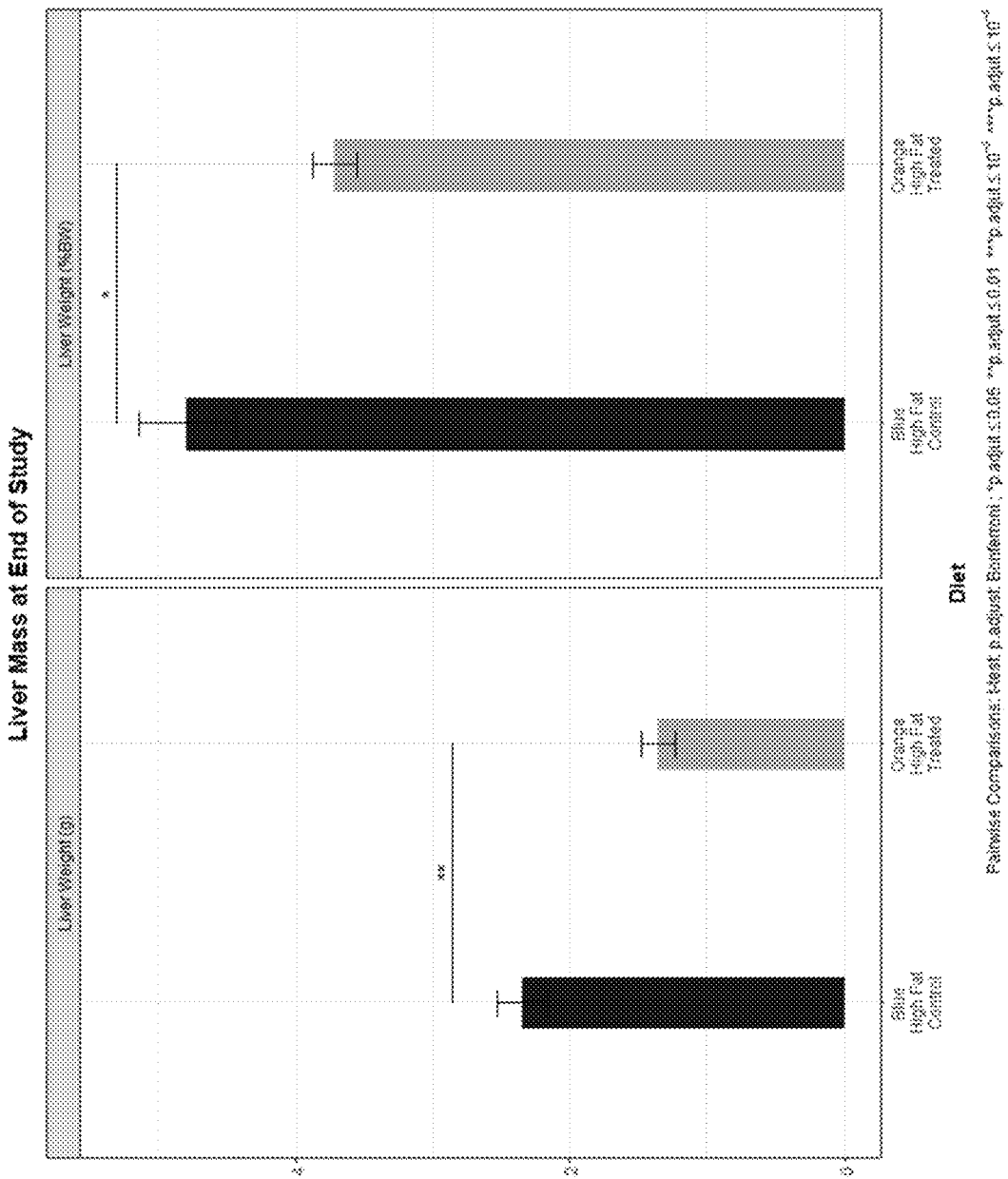
FIG. 3 is a series of bar graphs depicting the effect of treatment on liver weight of wild type mice fed a HFD over a 20-week period. Control mice (shown on left in each panel) were fed a HFD but not treated. Left panel shows absolute weight, right panel shows weight as a percentage of body weight.
Figure 4:
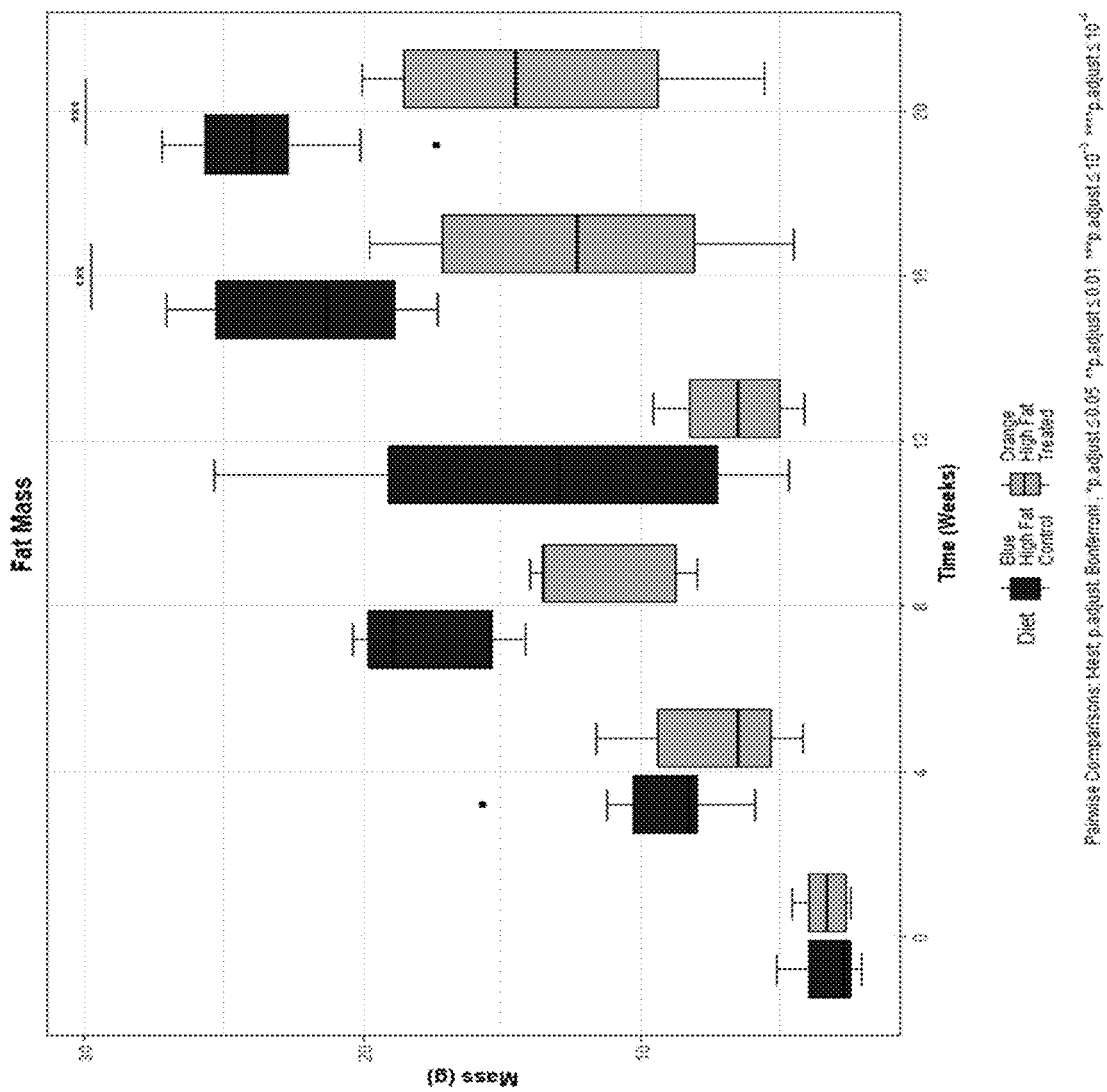
FIG. 4 is a graph depicting the effect of treatment or no-treatment on fat mass in wild type mice fed a HFD for 20 weeks. Boxes for treated mice are shown on the right at each time point.
Figure 5:
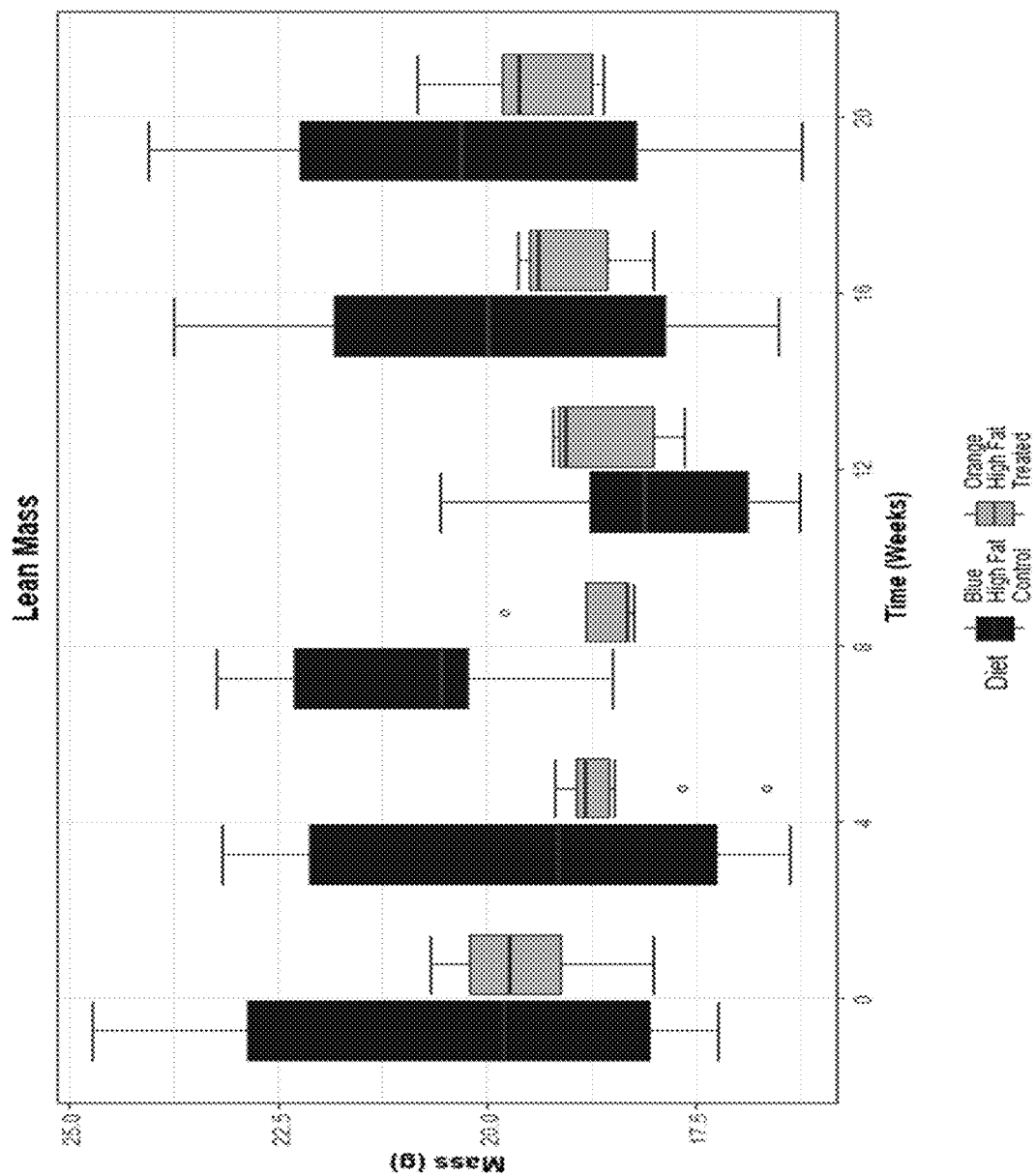
FIG. 5 is a graph depicting the effect of treatment or no-treatment on lean mass in wild type mice fed a HFD for 20 weeks. Boxes for treated mice are shown on the right at each time point.

Example 1C: Effects of Administration of a High-Fat Diet (HFD) Containing an Exemplary Composition on Wild-Type Mice with Diet-Induced Obesity Male wild-type C57BL/6 mice (Jackson Labs) that had already been made obese through administration of a chronic HFD were purchased. These mice when weighing a minimum of 40 g were then put on control HFD or treatment HFD. End points and measurements were the same as previous Examples. At this point, mice were randomly divided into one of two groups: 1) control or 2) treatment. All mice were fed a HFD consisting of 45% calories from lard (control diet). The treatment group had the same diet with the addition of the exemplary composition (Table 5). The following parameters were measured:
Body weight
Food intake
Body composition
Blood glucose
Plasma collected for future analysis
Glucose and insulin tolerance testing was conducted at intervals during the study
48 hr energy expenditure was conducted (CLAMS)
Faeces were collected during the CLAMS experiments
At termination, metabolic tissues were harvested, weighed, and collected for histology (formalin fixed) or frozen for future analysis (gene expression, metabolomics, proteomics) using standard techniques.
Results from this experiment are depicted in FIG. 2.

Figure 6:
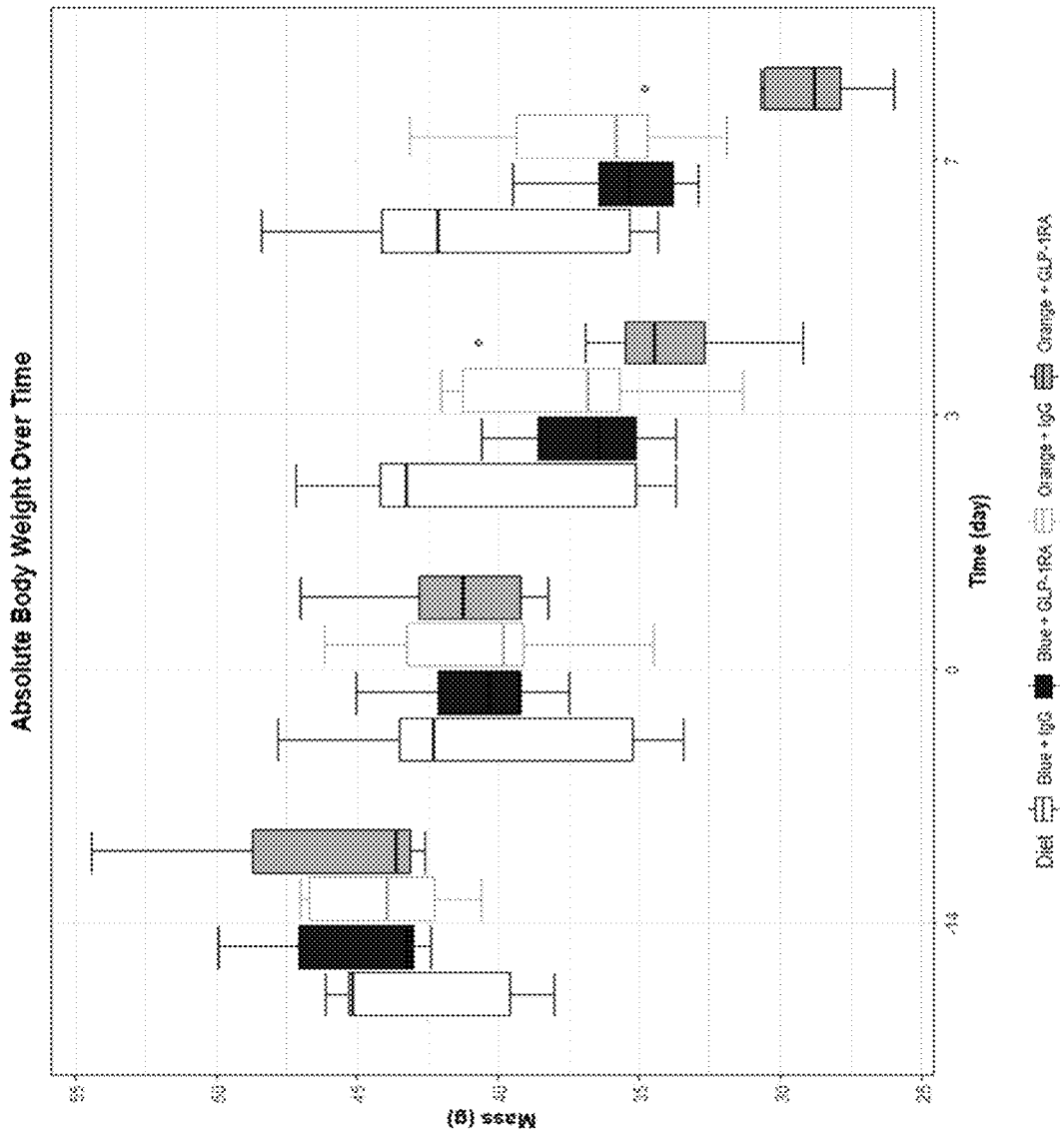
FIG. 6 is a graph depicting the effect of 7-day treatment (from time 0) alone or treatment combined with a GLP-1 agonist on body weight of DIO mice fed a 7-day HFD. Mice were treated with a GLP-1 agonist (GLP-1) (shaded boxes). Unshaded boxes indicate that mice were treated with control vehicle (IgG). Boxes for treated mice are shown on the right and second from right at each time point for animals treated with the combination of treatment and GLP-1.
Figure 7A:
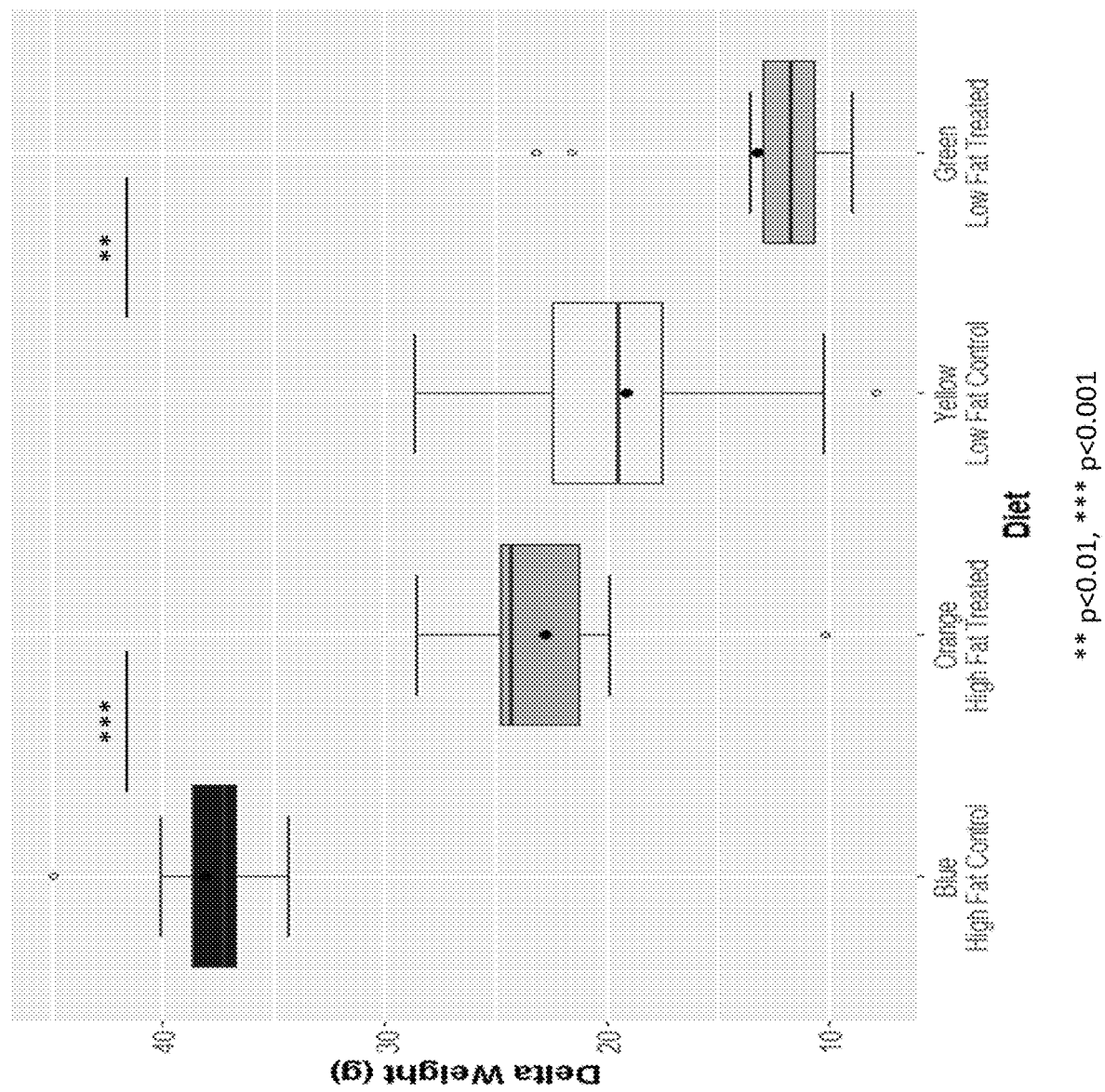
FIG. 7A-FIG. 7B depict the effect of treatment on weight loss in PS1E3 or PS1E4 mice fed either a HFD or a low-fat diet (LFD) for 20 weeks.
Figure 7B:
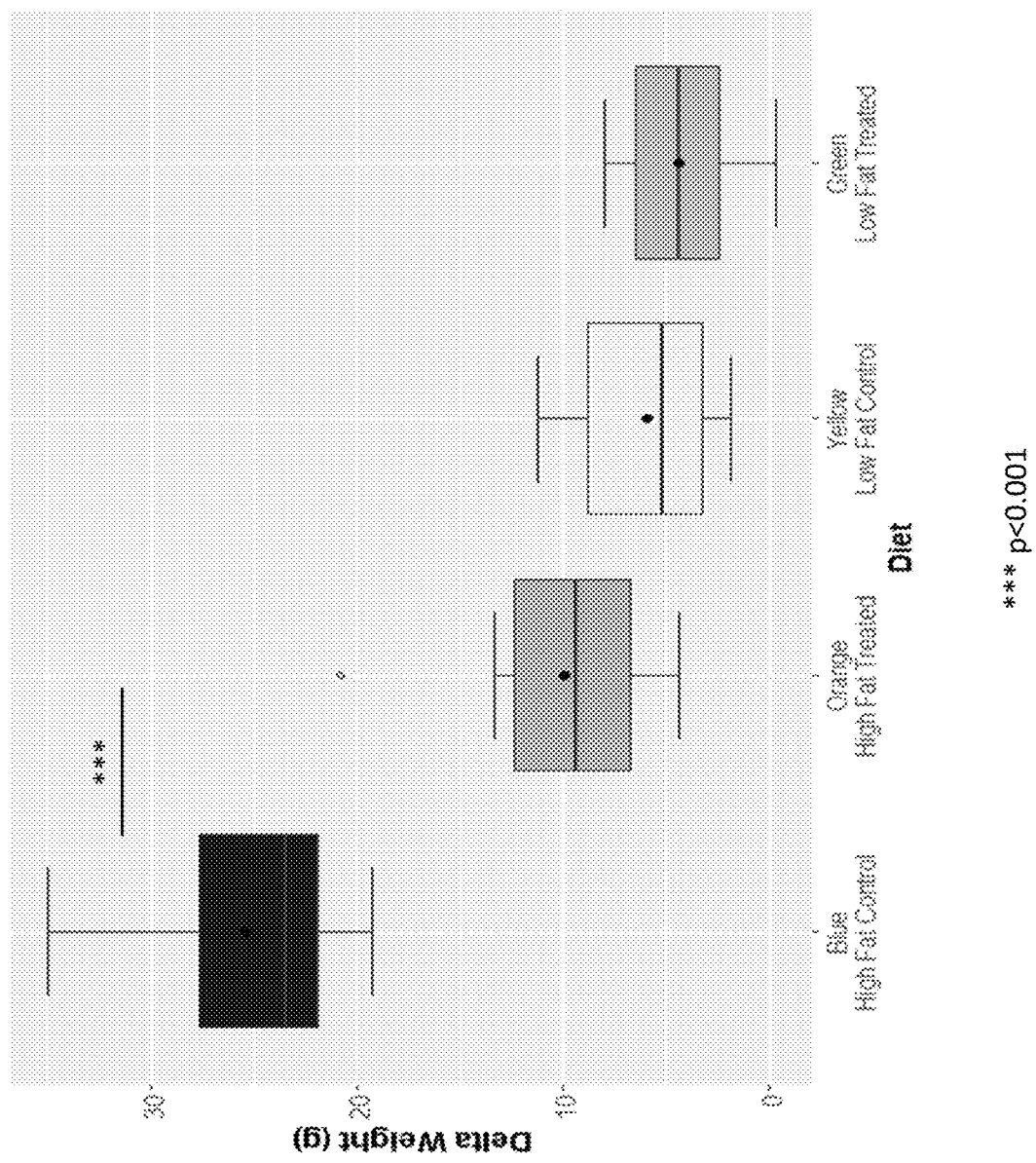
Figure 8:
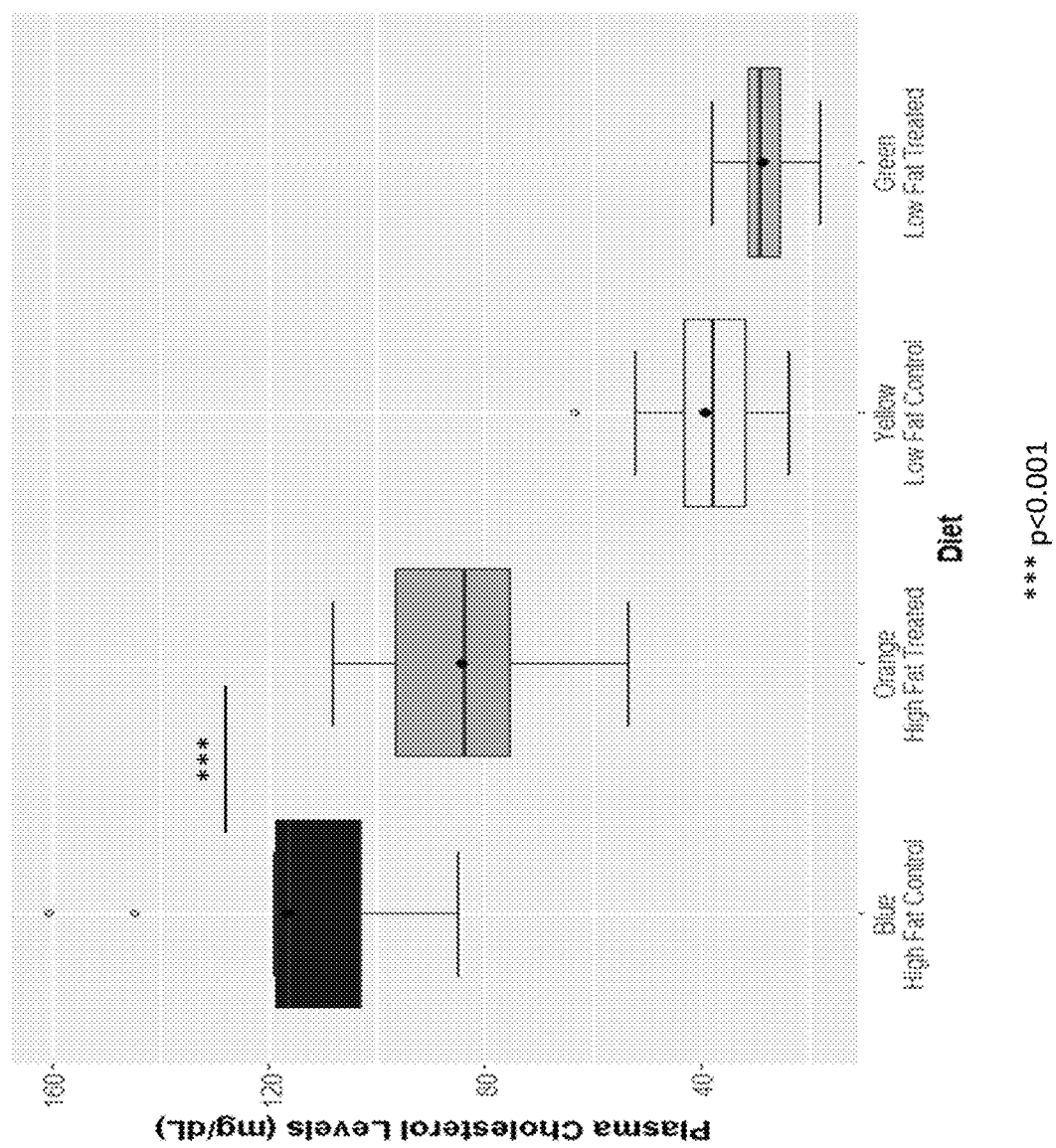
FIG. 8 depicts the effect of treatment on plasma cholesterol levels of PS1E3 mice fed either a HFD or a LFD over a 20-week period.
Figure 9:
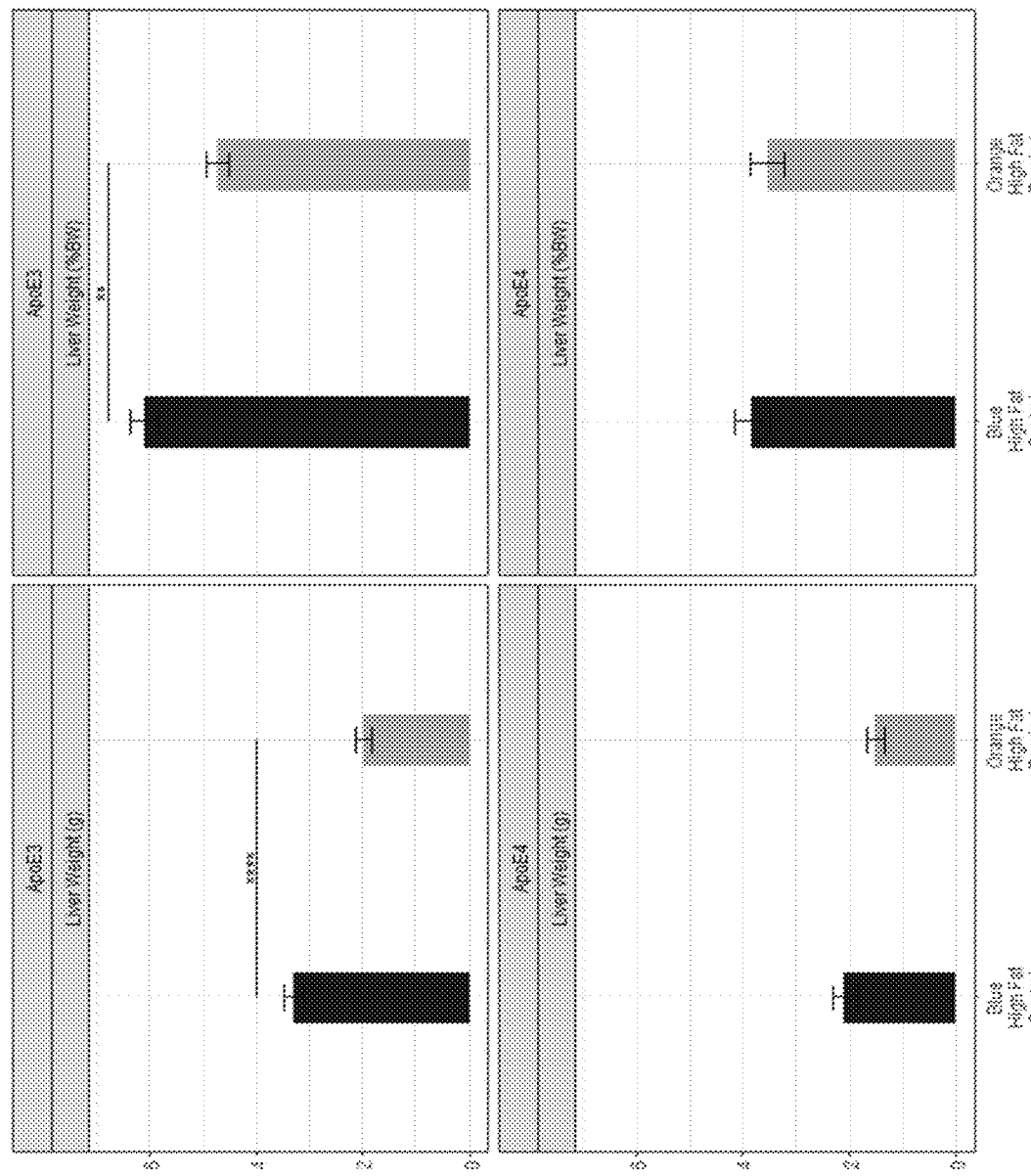
FIG. 9 depicts the effect of treatment or no treatment (control) on liver mass of ApoE3 and ApoE4 mice fed either a HFD or a LFD over a 20-week period.
Figure 10:
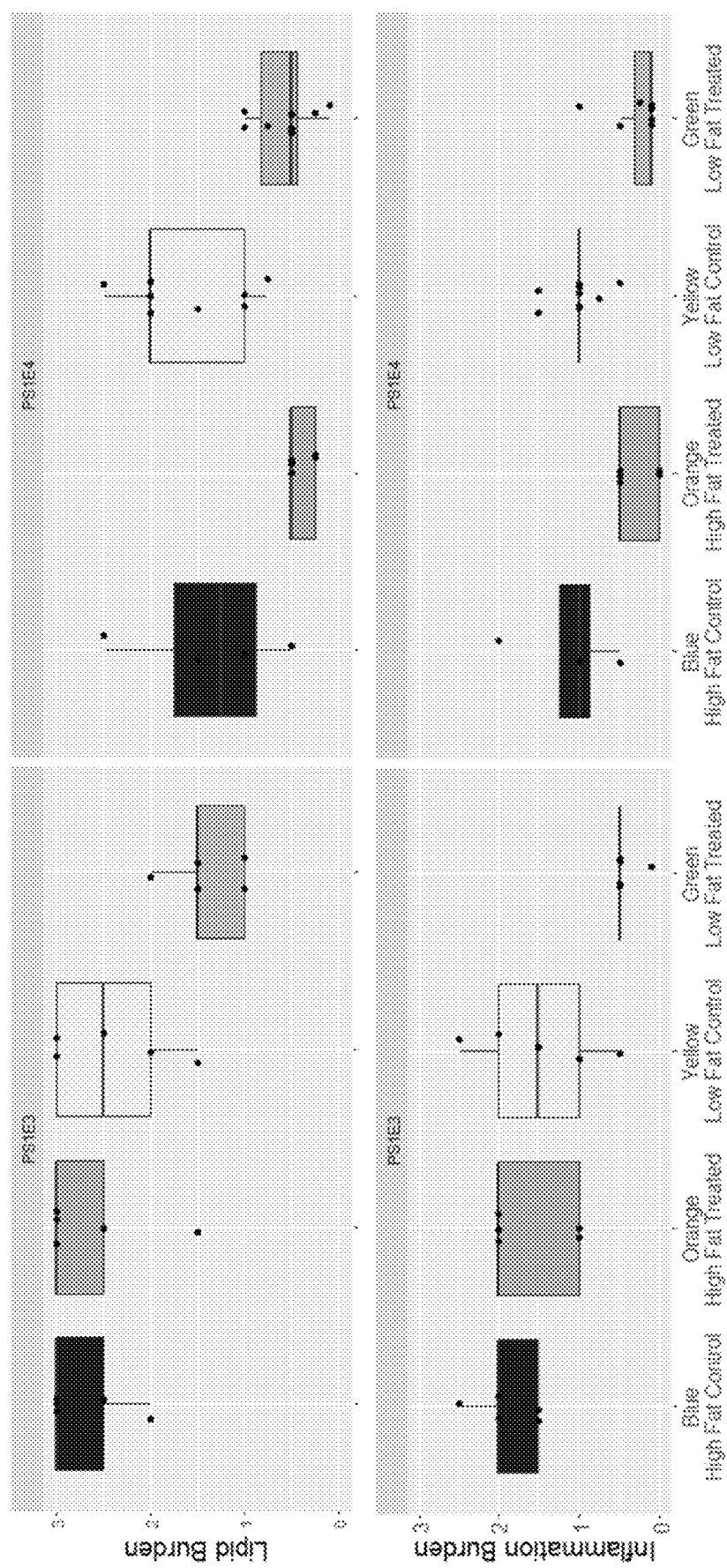
FIG. 10 depicts the effect of treatment or no treatment (control) on markers of NASH (non-alcoholic steatohepatitis) (lipid burden, inflammation, ballooning and necrosis) in PS1E3 or PS1E4 mice fed either HFD or LFD over a 20-week period.
Figure 11:
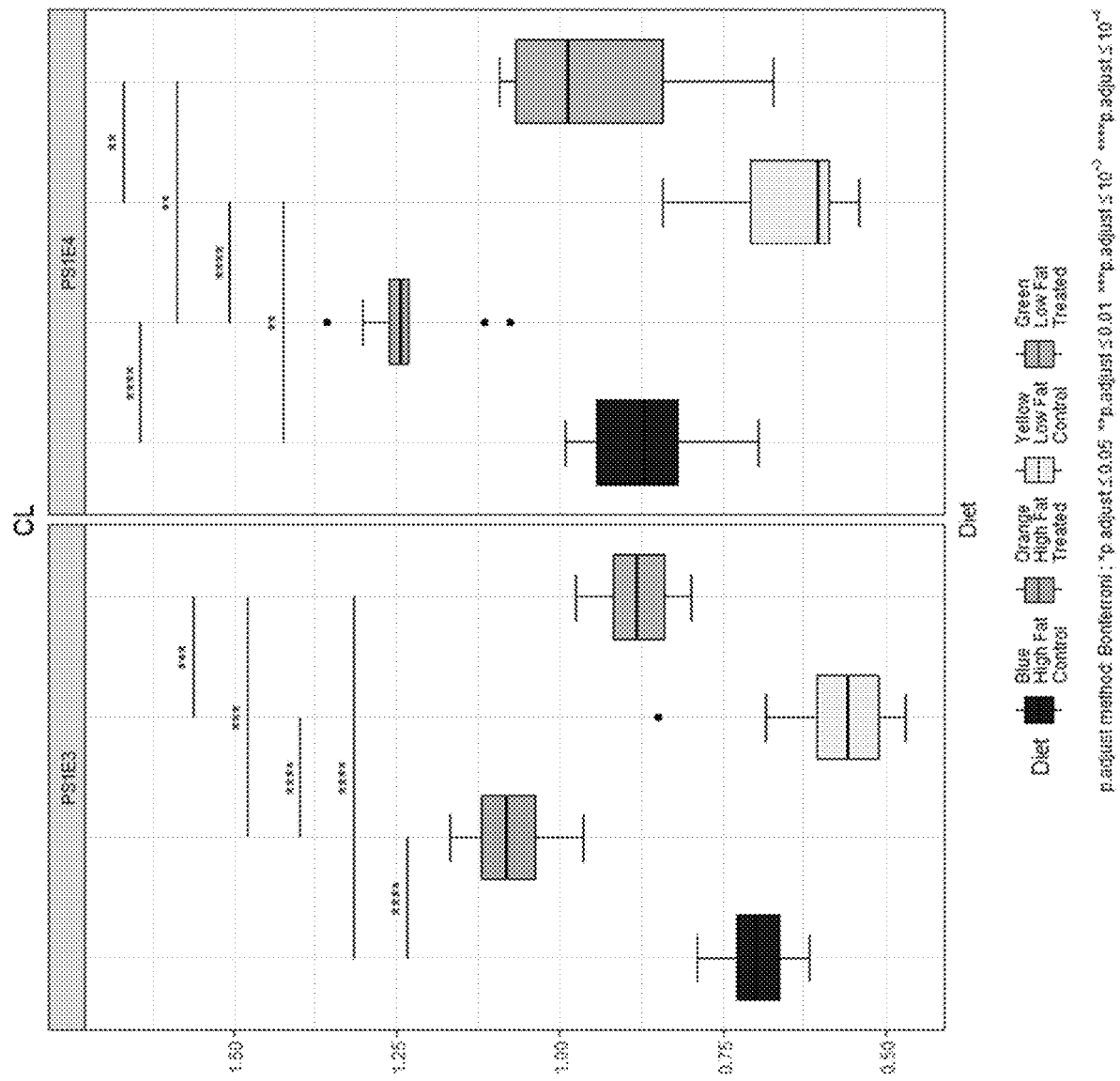
FIG. 11 depicts the effect of treatment or no treatment (control) on liver cardiolipin (CL) in PS1E3 or PS1E4 mice fed either HFD or LFD over a 20-week period.
Figure 12:
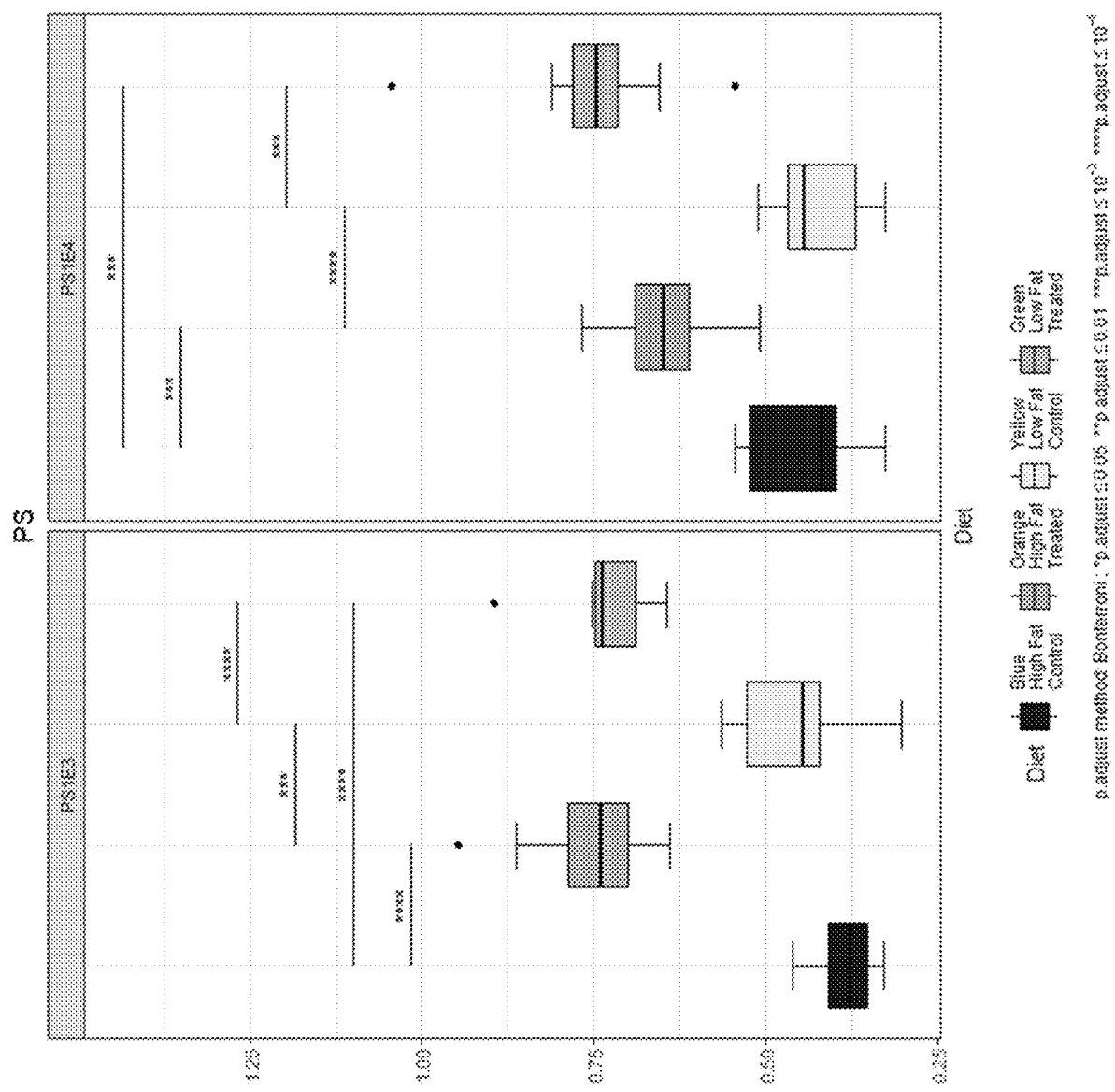
FIG. 12 depicts the effect of treatment or no treatment (control) on liver phosphatidylserine (PS) in PS1E3 or PS1E4 mice fed either a HFD or LFD over a 20-week period.
Figure 13:
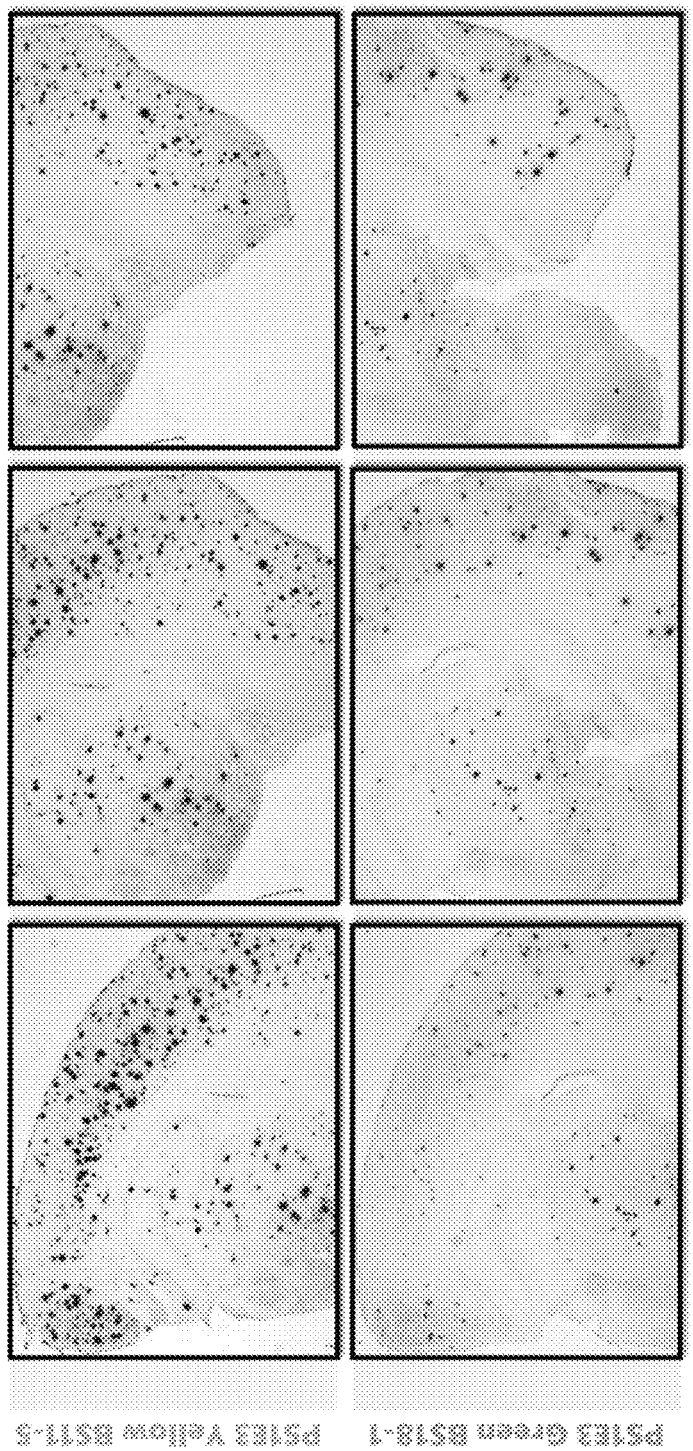
FIG. 13 depicts images showing the reduction in β-amyloid 42 hippocampal staining after 20 weeks of treatment (lower panels) in PS1E3 mice.
Figure 14:
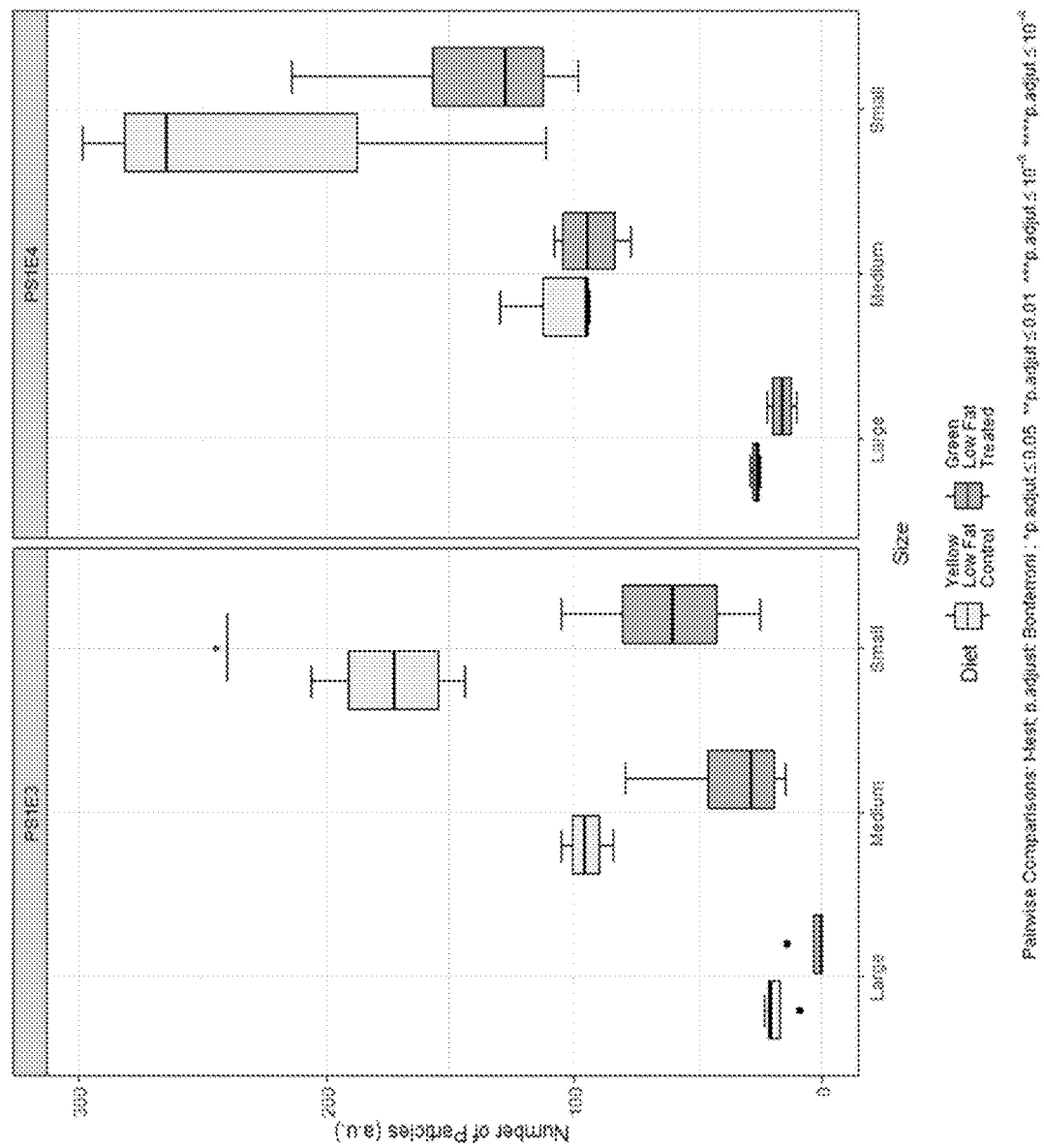
FIG. 14 depicts the effect of treatment or no treatment (control) on insoluble β-amyloid deposits in PS1E3 or PS1E4 mice over a 20-week period. Boxes for treated mice are shown in grey.
Figure 15:
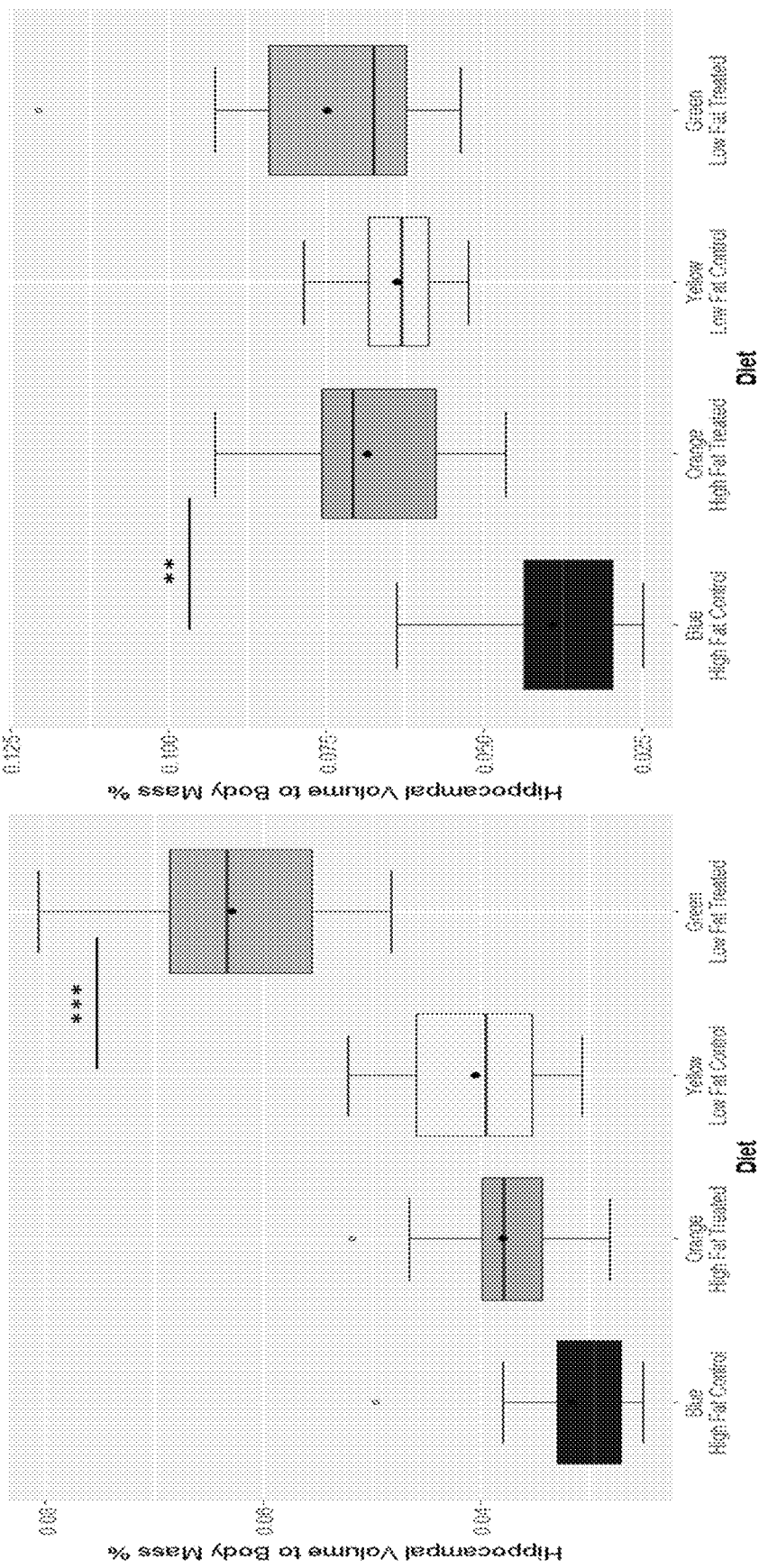
FIG. 15 depicts the effect of treatment or no treatment (control) on hippocampal mass relative to overall body mass in PS1E4 or PS1E3 mice fed either HFD or LFD over a 20-week period. Significant p-values p<0.05 are shown on the figure.
Figure 16:
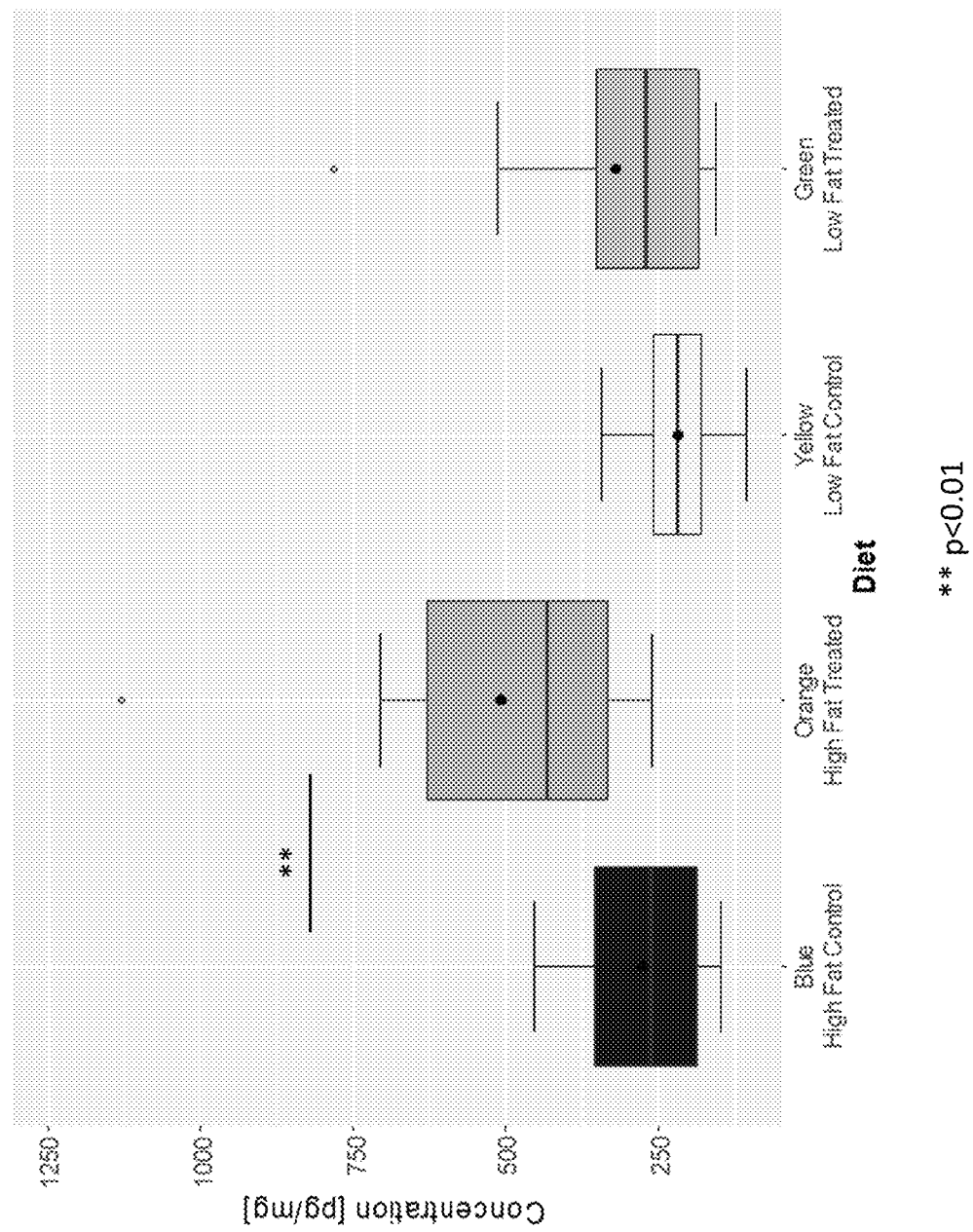
FIG. 16 depicts the effect of treatment or no treatment (control) on brain-derived neurotrophic factor (BDNF) levels in PS1E3 mice fed either HFD or LFD over a 20-week period. Significant p-values <0.05 are shown on the figure.
Figure 17:
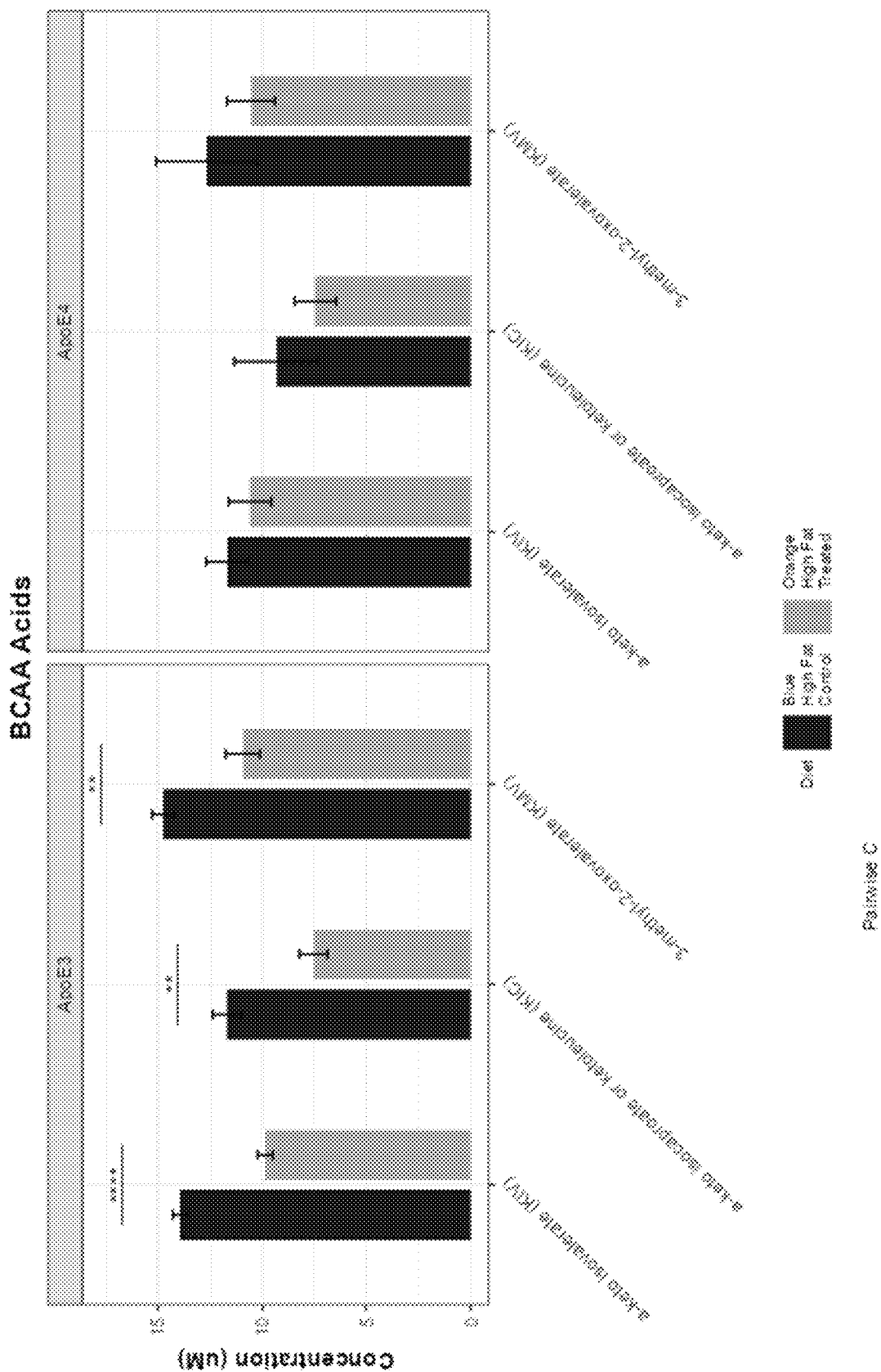
FIG. 17 depicts the effect of treatment or no treatment (control) on branch chain amino acid (BCAA) levels in APOE3 or APOE4 mice fed either HFD or LFD over a 20-week period. Pairwise comparisons: t-test; p.adjust: FDR; *p-adjut≤0.05; p-adjut≤0.01; *p-adjut≤$10^{-3}$; ****p-adjut≤$10^{-4}$.
Figure 18:
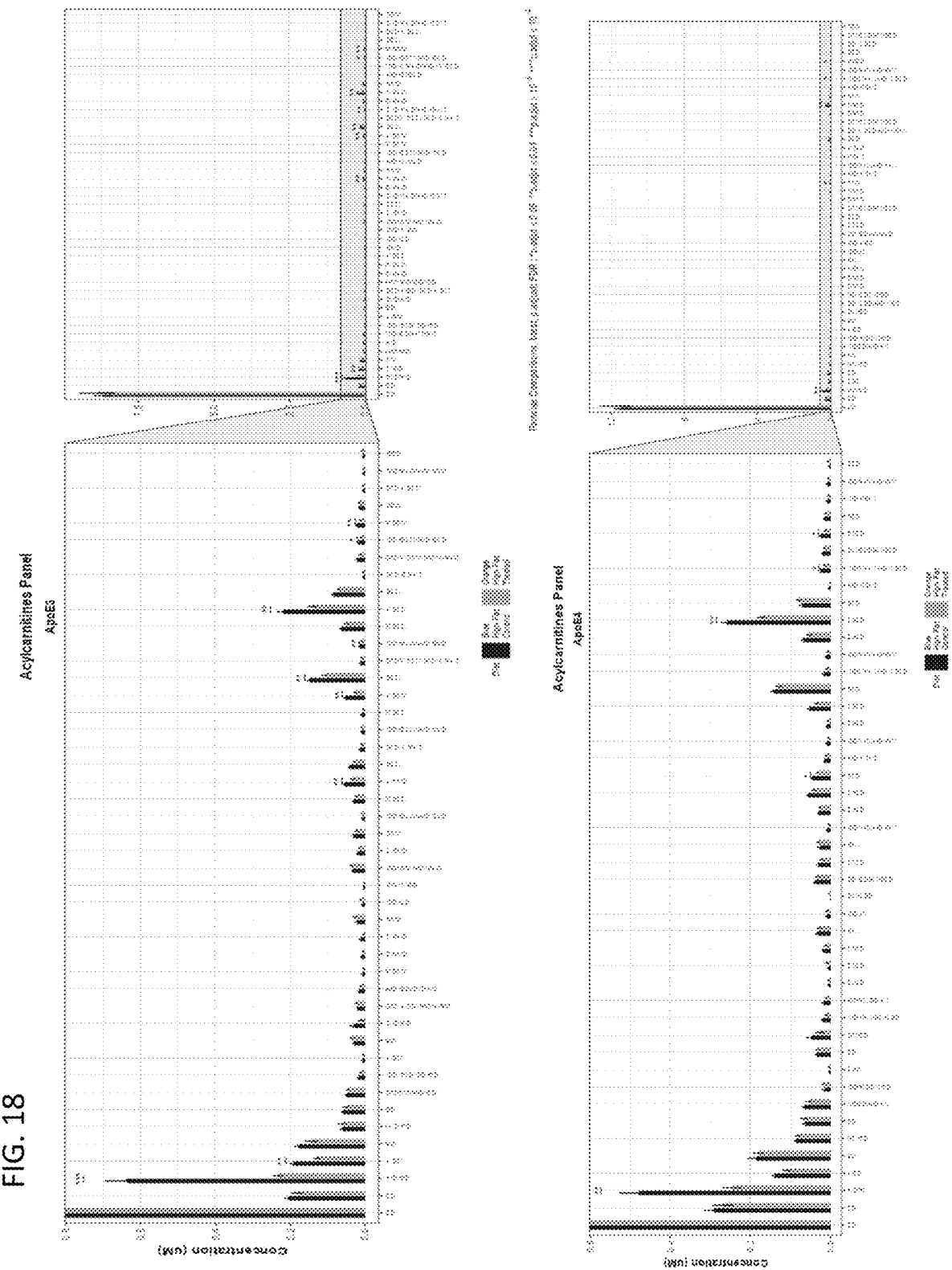
FIG. 18 depicts the effect of treatment or no treatment (control) on acylcarnitine levels in APOE3 or APOE4 mice fed either HFD or LFD over a 20-week period. Pairwise comparisons: t-test; p.adjust: FDR; *p-adjut≤0.05; p-adjut≤0.01; *p-adjut≤$10^{-3}$; ****p-adjut≤$10^{-4}$.

Example 1D: Effects of Administration of a High Fat Diet (HFD) Containing an Exemplary Composition and an Anti-Obesity Agent on Wild-Type Mice with Diet-Induced Obesity Male wild-type C57BL/6 mice (Jackson Labs) that had already been made obese through administration of a chronic HFD were purchased at 8-10 weeks of age and allowed to acclimate in the facility until 12 weeks of age. At this point, mice were randomly divided into one of three groups: 1) control, 2) treatment, 3) dulaglutide (GLP-1 agonist). All mice were fed a HFD consisting of 45% calories from lard (control diet). The treatment group were on the same diet with the addition of the exemplary composition (Table 5). The GLP-1 group received twice weekly injections of the GLP-1 agonist (10 mg/kg). Control and treatment groups received saline injections at the same time. The following parameters were measured:
Body weight
Food intake
Body composition
Blood glucose
Plasma collected for future analysis
Glucose and insulin tolerance testing was conducted at intervals during the study
48 hr energy expenditure was conducted (CLAMS)
faces were collected during the CLAMS experiments
At termination, metabolic tissues were harvested, weighed, and collected for histology (formalin fixed) or frozen for future analysis (gene expression, metabolomics, proteomics) using standard techniques.
Results from this experiment are depicted in FIG. 6.

Example 1E: Effects of Administration of a High Fat Diet (HFD) or a Low-Fat Diet (LFD) Containing an Exemplary Composition on APOE3-Expressing or APOE4-Expressing Mice Female APP/PS1/APOE3 (AE3 or PS1E3) or APP/PS1/APOE4 (AE4 or PS1E4) mice were used in these studies.

These mice are "targeted replacement" (TR) mice in which the endogenous murine ApoE gene has been replaced by the human ApoE3 or ApoE4 allele. This mouse model is described in Kouf et al., *J Clin Invest.* 1999; 103(11):1579-1586; Sullivan et al., *J Biol Chem.* 1997; 272(29):17972-80. These "human" ApoE ε3-TR or ApoE ε4-TR mice are then cross bred with $APP_{SW}/PS1_{-21}$ AD transgenic (Tog) model mice producing a complex model of APP/E3 and APP/E4 mice. The APOE ε3-TR or APOE F4-TR mice retain regulatory sequences as well as the endogenous control of the mouse ApoE gene and the noncoding murine exon 1 surrounding the inserted human exons 2', 3', and 4' and therefore, they express the human ApoE protein at physiological levels. This mouse model is described in Pankiewicz et al. *Molecular Neurodegeneration* (2017) 12:12.

Following weaning (at approximately 20-21 days), the animals were tagged with an ear pin for indentification and then underwent the removal of 1-2 mm of distal portion of tail for genotyping to confirm their transgenic status.

Female AE3 mice and AE4 mice were respectively group housed in plastic cages (4 animals per cage). Animals had access to the various diets (HFD or LFD) and water ad libitum. Animals were maintained on a 12-hour light/dark cycle with room temperature maintained at 22±2° C. and approximately 50% humidity.

Following weaning, animals were given access to the appropriate diet for up to 6 months. Date of birth and date of weaning were recorded. Animals had free ad-libitum access to the appropriate control or treatment diet. The treatment diets contained the exemplary composition (Table 5).

For the duration of the study, an observational battery was observed/measured and recorded every 2 weeks. The observational battery included at minimum:
Weight (including signs of body weight loss exceeding 15% of free-feeding body weight relative to an age-matched reference as well as differences in weight gain among various study cohorts)
Appearance of coat condition/hair loss
Signs of infection
Signs of moderate to severe pain or distress
Signs of behavioral change (including aggression, guarding, hiding, etc.)
Gait or movement Beginning at 3 months of age, blood samples were collected from the animals every 4 weeks for the duration of the study. Blood samples were used for plasma lipid analysis and to determine changes in metabolism. Blood samples were used to perform routine blood enzymatic testing using standard techniques that at a minimum included:
Total Cholesterol.
High Density Lipoprotein (HDL)
Triglycerides; and
Glucose After approximately 6 months post weaning and initiation of dietary access, terminal tissue collection included blood, brain, ascending aorta and left ventricle as well as liver harvesting.

After decapitation, animal brains were removed and dissected into 2 hemispheres. Upon initial dissection, each hemisphere was further micro-dissected into hippocampus (Hc), cortex (ctx) and cerebellum (Cb) sections. One hemisphere (with hippocampus (Hc), cortex (ctx) sections were drop fixed in formalin for immunocytochemical work, and the other hemisphere (with hippocampus (Hc), cortex (ctx) and cerebellum (Cb) sections) was immediately frozen in liquid nitrogen for protein/gene expression analysis.

Amyloid beta (Ab) protein ELISA's were performed to measure soluble levels of each Ab and ApoE protein species:
Soluble Total Aβ
Insoluble Total Aβ
Soluble Aβ42
Insoluble Aβ42
Soluble Aβ40
Insoluble Aβ40
ApoE ApoE protein Western Blot analysis was performed to evaluate structural and biophysical features or properties of ApoE protein:
Apolipoprotein E4 size, shape and proteolytic cleavage characteristics
Apolipoprotein E3 size, shape and proteolytic cleavage characteristics Histopathology and immunocytochemical staining were performed to measure:
Amyloid Plaques
Neuroinflammation (including Microglial Activation and/or Astrogliosis)
Synaptic Integrity
NAFLD/NASH
Atherosclerosis Tissue harvesting and formalin fixing for preservation:
Ascending Aorta and Left Atrium
Liver Sample Protein expression arrays were performed to measure levels of:
Amyloid beta degradation and clearance panel
Lipid/metabolic panel Results from this experiment are depicted in FIG. 7-FIG. 18.

Results Related to Effect of APOE Genotype on Responsiveness to Exemplary Composition Significantly lower total cholesterol levels were observed only in the treated APOE3 mice. Control fed APOE3 mice had significantly larger livers and liver fatty acid burden than APOE4 mice. Treatment significantly reduced liver weight and hepatic lipid burden. In the prevention studies (as well as in the Alzheimer's disease (AD)-related studies) treated APOE3 mice gained significantly less weight compared to treated APOE4 mice. There was a significant reduction in branch chain amino acid and acylcarnitine levels particularly in the APOE3 animals.

In the AD-related study, gross liver pathology showed that the treated APOE3 mice were more responsive to the composition. Significantly larger hippocampal volume differences were also observed in the treated APOE4 compared to APOE3 mice.

Figure 19:
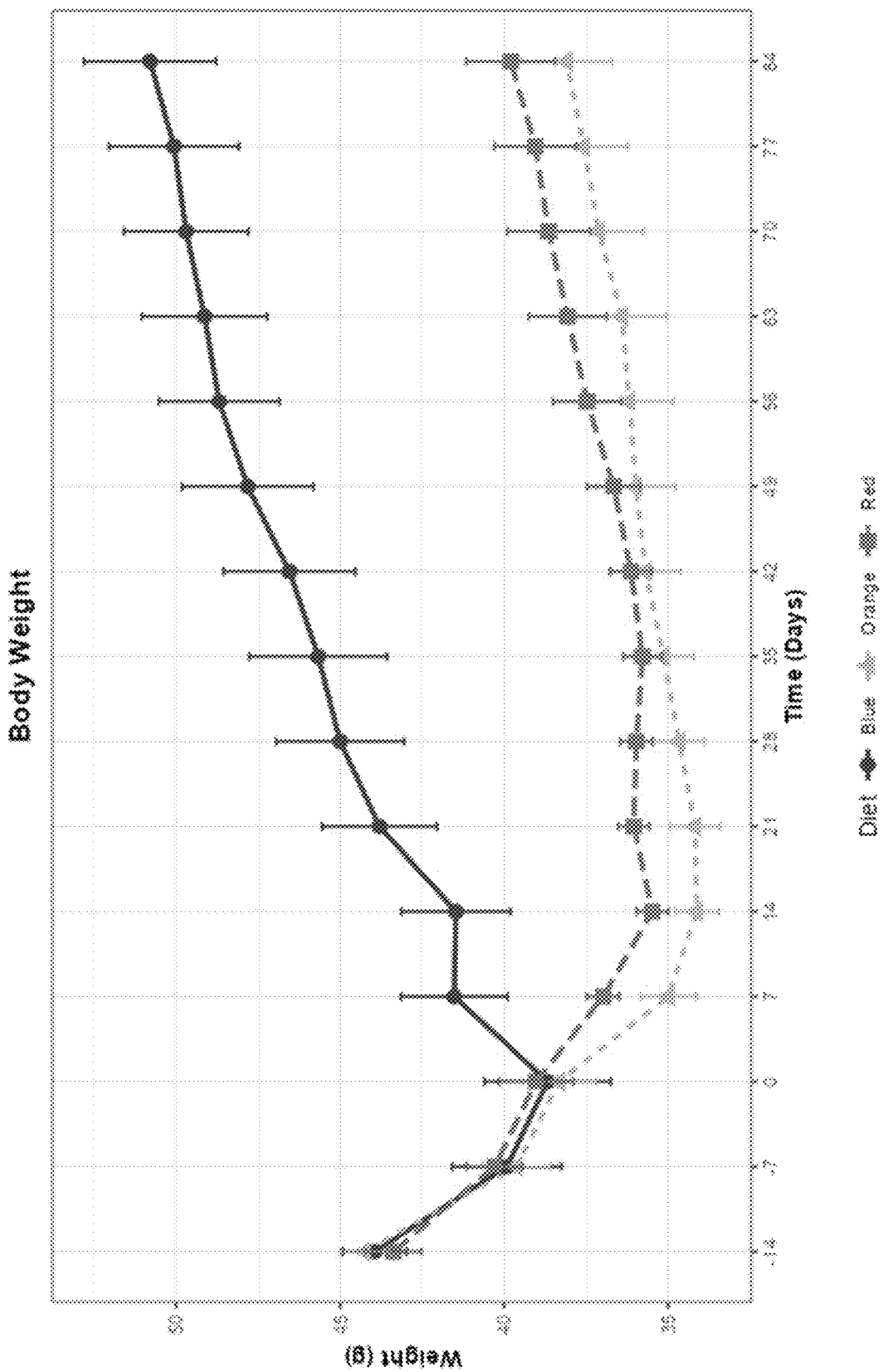
FIG. 19 depicts a graph showing the effect of a first treatment (triangle, nicotinic acid blend) or a second treatment (square, nicotinamide blend) on the body weight of wild type (diet-induced obesity) DIO mice maintained on a HFD over a 12-week period. Control (circle) DIO mice were maintained on a HFD but not treated.

Example 2: Effects of Nicotinic Acid Blend or Nicotinamide Blend on the Body Weight of Wild Type (Diet-Induced Obesity) DIO Mice Maintained on a HFD Over a 12-Week Period Niacin (also known as vitamin B3) is an essential nutrient found in a wide variety of foods including meats, poultry, and oily fish. Niacin has anti-inflammatory effects in various tissues including the brain and is a precursor of NADH. Niacin deficiency can lead to serious conditions such as pellagra, symptoms of which include diarrhea, inflammation, and cognitive deficits. Niacin comes in several forms, e.g., nicotinic acid or nicotinamide. In man nicotinic acid can cause "flushing" and peripheral vasodilation as well as being a precursor of NADH. Nicotinamide also acts as a precursor of NADH, involved in cellular energy metabolism, without the unwanted "flush". Our data shows nicotinic acid and nicotinamide have comparable effects in the diet-induced obesity mouse model (see FIG. 19), suggesting that the beneficial effect of including niacin in the treatments disclosed herein is not due to the vasodilatory effects. Results of this experiment are depicted in FIG. 19.

Every document cited herein, including any cross-referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the disclosure have been illustrated and described, various other changes and modifications can be made without departing from the spirit and scope of the disclosure. The scope of the appended claims includes all such changes and modifications that are within the scope of this disclosure.

What is claimed is:

1. A method for lessening or diminishing a symptom of Alzheimer's disease in a subject in need thereof, the method comprising:
    administering to the subject an effective amount of a composition comprising:
        (a) niacin, or a pharmaceutically acceptable salt thereof;
        (b) berberine, or a pharmaceutically acceptable salt thereof;
        (c) silymarin, silibinin, or Siliphos® (formulated silibinin), or any combination thereof, or a pharmaceutically acceptable salt thereof;
        (d) lipoic acid, or a pharmaceutically acceptable salt thereof;
        (e) taurine, or a pharmaceutically acceptable salt thereof, and
        (f) phospholipid or a pharmaceutically acceptable salt thereof;
    wherein the silymarin, silibinin, Siliphos® (formulated silibinin), any combination thereof, or the pharmaceutically acceptable salt thereof, is complexed with the phospholipid;
    wherein the niacin, or the pharmaceutically acceptable salt thereof, is in an amount from about 20% to about 40% by weight;
    wherein the berberine, or the pharmaceutically acceptable salt thereof, is in an amount from about 10% to about 20% by weight;
    wherein the silymarin, or the pharmaceutically acceptable salt thereof, the silibinin, or the pharmaceutically acceptable salt thereof, and/or the Siliphos® (formulated silibinin), or the pharmaceutically acceptable salt thereof, combined, are in an amount from about 8% to about 20% by weight;
    wherein the lipoic acid, or the pharmaceutically acceptable salt thereof, is in an amount from about 5% to about 15% by weight;
    wherein the taurine, or the pharmaceutically acceptable salt thereof, is in an amount from about 20% to about 35% by weight; and
    wherein the phospholipid, or the pharmaceutically acceptable salt thereof, is in an amount selected from about 5% to about 20% by weight.

2. The method of claim 1, wherein the symptom of Alzheimer's disease is a memory defect or dementia.

3. The method of claim 1, wherein the method further comprises determining that the subject has one or two APOE4 alleles or one or two APOE3 alleles of the apolipoprotein E gene before administering the composition to the subject.

4. The method of claim 1, wherein the method further comprises determining a level of acylcarnitines and/or branched-chain keto acids in the subject after administering the composition.

5. The method of claim 1, wherein the niacin is in the form of vitamin B3, nicotinic acid, nicotinamide, inositol hexanicotinate, nicotinic riboside, nicotinamide adenine dinucleotide (NAD), or NADH.

6. The method of claim 1, wherein the berberine, or the pharmaceutically acceptable salt thereof is complexed with the phospholipid.

7. The method of claim 1, wherein the phospholipid, or the pharmaceutically acceptable salt thereof, is in a complex with one or more of:
    the niacin, or the pharmaceutically acceptable salt thereof,
    the berberine, or the pharmaceutically acceptable salt thereof;
    the lipoic acid, or the pharmaceutically acceptable salt thereof, and
    the taurine, or the pharmaceutically acceptable salt thereof.

8. The method of claim 1, wherein the components (a) to (e) of the composition comprise:
    (i) about 250 mg niacin, or a pharmaceutically acceptable salt thereof, about 250 mg berberine, or a pharmaceutically acceptable salt thereof, about 150 mg silymarin, silibinin, or Siliphos® (formulated silibinin), or any combination thereof, or a pharmaceutically acceptable salt thereof; about 150 mg lipoic acid, or a pharmaceutically acceptable salt thereof; and about 375 mg taurine, or a pharmaceutically acceptable salt thereof,
    (ii) about 500 mg niacin, or a pharmaceutically acceptable salt thereof, about 250 mg berberine, or a pharmaceutically acceptable salt thereof, about 150 mg silymarin, silibinin, or Siliphos® (formulated silibinin), or any combination thereof, or a pharmaceutically acceptable salt thereof; about 150 mg lipoic acid, or a pharmaceutically acceptable salt thereof; and about 375 mg taurine, or a pharmaceutically acceptable salt thereof,
    (iii) about 1000 mg niacin, or a pharmaceutically acceptable salt thereof, about 500 mg berberine, or a pharmaceutically acceptable salt thereof, about 300 mg silymarin, silibinin, or Siliphos® (formulated silibinin), or any combination thereof, or a pharmaceutically acceptable salt thereof; about 300 mg lipoic acid, or a pharmaceutically acceptable salt thereof; and about 750 mg taurine, or a pharmaceutically acceptable salt thereof, or
    (iv) about 2000 mg niacin, or a pharmaceutically acceptable salt thereof; about 750 mg berberine, or a pharmaceutically acceptable salt thereof, about 450 mg silymarin, silibinin, or Siliphos® (formulated silibinin), or any combination thereof, or a pharmaceutically acceptable salt thereof; about 600 mg lipoic acid, or a pharmaceutically acceptable salt thereof; and about 1500 mg taurine, or a pharmaceutically acceptable salt thereof.

9. The method of claim 1, wherein the phospholipid is phosphatidylcholine.

10. The method of claim 1, wherein the composition further comprises a pharmaceutically acceptable carrier, diluent, excipient, or flavoring.

11. The method of claim 1, wherein the composition is orally administered to the subject twice daily, daily, weekly, biweekly, or monthly.

12. A method for lessening or diminishing a symptom of Alzheimer's disease in a subject in need thereof, the method comprising:
   (i) determining that the subject has one or two APOE4 alleles or one or two APOE3 alleles of the apolipoprotein E gene before administering a composition to the subject; and
   (ii) administering to the subject an effective amount of the composition comprising:
      (a) niacin, or a pharmaceutically acceptable salt thereof;
      (b) berberine, or a pharmaceutically acceptable salt thereof;
      (c) silymarin, silibinin, or Siliphos® (formulated silibinin), or any combination thereof, or a pharmaceutically acceptable salt thereof;
      (d) lipoic acid, or a pharmaceutically acceptable salt thereof;
      (e) taurine, or a pharmaceutically acceptable salt thereof, and
      (f) phospholipid or a pharmaceutically acceptable salt thereof;
   wherein the silymarin, silibinin, Siliphos® (formulated silibinin), any combination thereof, or pharmaceutically acceptable salt thereof, is complexed with the phospholipid;
   wherein the niacin, or the pharmaceutically acceptable salt thereof, is in an amount from about 20% to about 40% by weight;
   wherein the berberine, or the pharmaceutically acceptable salt thereof, is in an amount from about 10% to about 20% by weight;
   wherein the silymarin, or the pharmaceutically acceptable salt thereof, the silibinin, or the pharmaceutically acceptable salt thereof, and/or the Siliphos® (formulated silibinin), or the pharmaceutically acceptable salt thereof, combined, are in an amount from about 8% to about 20% by weight;
   wherein the lipoic acid, or the pharmaceutically acceptable salt thereof, is in an amount from about 5% to about 15% by weight;
   wherein the taurine, or the pharmaceutically acceptable salt thereof, is in an amount from about 20% to about 35% by weight; and
   wherein the phospholipid, or the pharmaceutically acceptable salt thereof, is in an amount selected from about 5% to about 20% by weight.

13. A method for producing a composition, the method comprising mixing components of (a)-(f):
   (a) niacin, or a pharmaceutically acceptable salt thereof;
   (b) berberine, or a pharmaceutically acceptable salt thereof;
   (c) silymarin, silibinin, or Siliphos® (formulated silibinin), or any combination thereof, or a pharmaceutically acceptable salt thereof;
   (d) lipoic acid, or a pharmaceutically acceptable salt thereof;
   (e) taurine, or a pharmaceutically acceptable salt thereof, and
   (f) phospholipid or a pharmaceutically acceptable salt thereof;
   wherein the silymarin, silibinin, Siliphos® (formulated silibinin), any combination thereof, or pharmaceutically acceptable salt thereof, is complexed with the phospholipid; wherein the niacin, or the pharmaceutically acceptable salt thereof, is in an amount from about 20% to about 40% by weight;
   wherein the berberine, or the pharmaceutically acceptable salt thereof, is in an amount from about 10% to about 20% by weight;
   wherein the silymarin, or the pharmaceutically acceptable salt thereof, the silibinin, or the pharmaceutically acceptable salt thereof, and/or the Siliphos® (formulated silibinin), or the pharmaceutically acceptable salt thereof, combined, are in an amount from about 8% to about 20% by weight;
   wherein the lipoic acid, or the pharmaceutically acceptable salt thereof, is in an amount from about 5% to about 15% by weight;
   wherein the taurine, or the pharmaceutically acceptable salt thereof, is in an amount from about 20% to about 35% by weight; and
   wherein the phospholipid, or the pharmaceutically acceptable salt thereof, is in an amount selected from about 5% to about 20% by weight.

14. The method of claim 13, wherein the berberine or the pharmaceutically acceptable salt thereof is complexed with the phospholipid.

15. The method of claim 13, wherein the components of (a)-(f) are further placed in a capsule or formulated into a tablet after mixing.

16. The method of claim 13, wherein the components of (a)-(f) are mixed as a blend and subsequently dissolved in water to produce an aqueous composition.

17. The method of claim 13, wherein the components of (a)-(f) are added sequentially to water to produce an aqueous composition.

18. The method of claim 16, wherein the aqueous composition is further filtered and/or heat pasteurized.

19. The method of claim 16, wherein the aqueous composition is further aliquoted into dosage forms.

20. The method of claim 16, wherein the aqueous composition is not heat pasteurized.

21. The method of claim 20, wherein the aqueous composition is further used to cold-fill a bottle or a package.

22. A method for enhancing the efficacy of an anti-obesity agent used for lessening or diminishing obesity in a subject in need thereof, the method comprising:
   (i) administering to the subject the anti-obesity agent and an effective amount of a composition comprising:
      (a) niacin, or a pharmaceutically acceptable salt thereof;
      (b) berberine, or a pharmaceutically acceptable salt thereof;
      (c) silymarin, silibinin, or Siliphos® (formulated silibinin), or any combination thereof, or a pharmaceutically acceptable salt thereof;
      (d) lipoic acid, or a pharmaceutically acceptable salt thereof;
      (e) taurine, or a pharmaceutically acceptable salt thereof, and
      (f) phospholipid or a pharmaceutically acceptable salt thereof;

wherein the silymarin, silibinin, Siliphos® (formulated silibinin), any combination thereof, or a pharmaceutically acceptable salt thereof, is complexed with the phospholipid;

wherein the niacin, or the pharmaceutically acceptable salt thereof, is in an amount from about 20% to about 40% by weight;

wherein the berberine, or the pharmaceutically acceptable salt thereof, is in an amount from about 10% to about 20% by weight;

wherein the silymarin, or the pharmaceutically acceptable salt thereof, the silibinin, or the pharmaceutically acceptable salt thereof, and/or the Siliphos® (formulated silibinin), or the pharmaceutically acceptable salt thereof, combined, are in an amount from about 8% to about 20% by weight;

wherein the lipoic acid, or the pharmaceutically acceptable salt thereof, is in an amount from about 5% to about 15% by weight;

wherein the taurine, or the pharmaceutically acceptable salt thereof, is in an amount from about 20% to about 35% by weight; and wherein the phospholipid, or the pharmaceutically acceptable salt thereof, is in an amount selected from about 5% to about 20% by weight; and (ii) determining a level of acylcarnitines and/or branched chain keto acids in the subject after administering the composition.

* * * * *